US012690911B2

(12) United States Patent
Boudreaux et al.

(10) Patent No.: US 12,690,911 B2
(45) Date of Patent: Jul. 28, 2026

(54) ELECTROSURGICAL INSTRUMENT WITH LIGHT ACCUMULATOR END EFFECTOR AND FIBER OPTICS

(71) Applicant: Cilag GmbH International, Zug (CH)

(72) Inventors: Chad P. Boudreaux, Cincinnati, OH (US); Narendran Narasimhan, Cincinnati, OH (US); Thomas J. Watson, Over (GB)

(73) Assignee: CILAG GMBH INTERNATIONAL, Zug (CH)

( * ) Notice: Subject to any disclaimer, the term of this patent is extended or adjusted under 35 U.S.C. 154(b) by 893 days.

(21) Appl. No.: 17/490,060

(22) Filed: Sep. 30, 2021

(65) Prior Publication Data

US 2023/0096074 A1     Mar. 30, 2023

(51) Int. Cl.
*A61B 18/14* (2006.01)
*A61B 90/30* (2016.01)
*A61B 18/00* (2006.01)

(52) U.S. Cl.
CPC .......... *A61B 18/1445* (2013.01); *A61B 90/30* (2016.02); *A61B 2018/00601* (2013.01);
(Continued)

(58) Field of Classification Search
CPC ................ A61B 18/1445; A61B 90/30; A61B 2018/00601; A61B 2018/00773; A61B 2090/306; A61B 2017/00057; A61B 2018/00345; A61B 2018/00619; A61B 2018/0063; A61B 2562/0238; A61B 18/1442; A61B 18/1447; A61B 2018/1442; A61B 2018/145; A61B 2018/1452; A61B 2018/1455; A61B 2018/1457; A61B 2018/146; A61B 2018/1462; A61B 17/28; A61B 17/2804; A61B 2017/2808; A61B 17/2812; A61B 17/2816; A61B 17/282; A61B 2017/2825; A61B 2017/2829;
(Continued)

(56) References Cited

U.S. PATENT DOCUMENTS 6,500,176 B1   12/2002   Truckai et al.
6,783,524 B2   8/2004    Anderson et al.
(Continued)

FOREIGN PATENT DOCUMENTS

EP          3047806 A1 *   7/2016    ....... A61B 17/00234

OTHER PUBLICATIONS

International Search Report and Written Opinion dated Dec. 8, 2022 for Application No. PCT/IB2022/059162, 14 pages.

*Primary Examiner* — Joanne M Rodden
*Assistant Examiner* — Dana Stumpfoll
(74) *Attorney, Agent, or Firm* — FBT Gibbons LLP

(57) ABSTRACT

A surgical instrument includes a shaft assembly having a distal end and an end effector at the distal end of the shaft assembly. The end effector includes a first jaw and a second jaw movably coupled relative to the first jaw for clamping tissue therebetween. The end effector also includes at least one lightbox for detecting the tissue. The at least one lightbox includes a housing having at least one optically transmissive surface configured to face the tissue. The at least one lightbox also includes at least one of an illuminating element or a light receiving element. The at least one of an illuminating element or a light receiving element is secured to the housing.

20 Claims, 17 Drawing Sheets

(52) U.S. Cl.
CPC ............... *A61B 2018/00773* (2013.01); *A61B 2090/306* (2016.02)

(58) Field of Classification Search
CPC ........ A61B 17/2833; A61B 2017/2837; A61B 17/2841; A61B 2017/2845; A61B 17/285; A61B 17/29; A61B 2017/2901; A61B 2017/2902; A61B 2017/2903; A61B 2017/2904; A61B 2017/2905; A61B 2017/2906; A61B 2017/2908; A61B 17/2909; A61B 2017/291; A61B 2017/2911; A61B 2017/2912; A61B 2017/2913; A61B 2017/2915; A61B 2017/2916; A61B 2017/2917; A61B 2017/2918; A61B 2017/2919; A61B 2017/292; A61B 2017/2922; A61B 2017/2923; A61B 2017/2924; A61B 2017/2925; A61B 2017/2926; A61B 2017/2929; A61B 2017/293; A61B 2017/2931; A61B 2017/2932; A61B 2017/2933; A61B 2017/2934; A61B 2017/2936; A61B 2017/2937; A61B 2017/2938; A61B 2017/2939; A61B 2017/294; A61B 2017/2941; A61B 2017/2943; A61B 2017/2944; A61B 2017/2945; A61B 2017/2946; A61B 2017/2947; A61B 2017/2948; A61B 17/295; A61B 17/30; A61B 2017/301; A61B 2017/303; A61B 2017/305; A61B 2017/306; A61B 2017/308
See application file for complete search history.

(56) References Cited

U.S. PATENT DOCUMENTS

| | | | |
|---|---|---|---|
| 8,888,809 B2 | 11/2014 | Davison et al. | |
| 8,939,974 B2 | 1/2015 | Boudreaux et al. | |
| 8,986,302 B2 | 3/2015 | Aldridge et al. | |
| 9,149,325 B2 | 10/2015 | Worrell et al. | |
| 9,161,803 B2 | 10/2015 | Yates et al. | |
| 9,526,565 B2 | 12/2016 | Strobl | |
| 9,545,253 B2 | 1/2017 | Worrell et al. | |
| 9,877,720 B2 | 1/2018 | Worrell et al. | |
| 9,877,782 B2 | 1/2018 | Voegele et al. | |
| 2011/0251605 A1 | 10/2011 | Hoarau et al. | |
| 2012/0296205 A1 | 11/2012 | Chernov et al. | |
| 2013/0253489 A1* | 9/2013 | Nau, Jr. | A61B 18/22 606/17 |
| 2016/0346034 A1* | 12/2016 | Arya | A61B 18/22 |
| 2018/0214209 A1* | 8/2018 | Nau, Jr. | A61B 17/282 |
| 2019/0053691 A1* | 2/2019 | Hansen | A61B 17/29 |
| 2023/0100459 A1 | 3/2023 | Draginoff, Jr. et al. | |
| 2023/0101623 A1 | 3/2023 | Boudreaux et al. | |

* cited by examiner

ELECTROSURGICAL INSTRUMENT WITH LIGHT ACCUMULATOR END EFFECTOR AND FIBER OPTICS

BACKGROUND

A variety of surgical instruments include a tissue cutting element and one or more elements that transmit radio frequency (RF) energy to tissue (e.g., to coagulate or seal the tissue). An example of such an electrosurgical instrument is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein, in its entirety; U.S. Pat. No. 8,939,974, entitled "Surgical Instrument Comprising First and Second Drive Systems Actuatable by a Common Trigger Mechanism," issued Jan. 27, 2015, the disclosure of which is incorporated by reference herein, in its entirety; U.S. Pat. No. 8,888,809, entitled "Surgical Instrument with Jaw Member," issued Nov. 18, 2014, the disclosure of which is incorporated by reference herein, in its entirety; U.S. Pat. No. 9,161,803, entitled "Motor Driven Electrosurgical Device with Mechanical and Electrical Feedback," issued Oct. 20, 2015, the disclosure of which is incorporated by reference herein, in its entirety; U.S. Pat. No. 9,877,720, entitled "Control Features for Articulating Surgical Device," issued Jan. 30, 2018, the disclosure of which is incorporated by reference herein, in its entirety; U.S. Pat. No. 9,545,253, entitled "Surgical Instrument with Contained Dual Helix Actuator Assembly," issued Jan. 17, 2017, the disclosure of which is incorporated by reference herein, in its entirety; and U.S. Pat. No. 9,526,565, entitled "Electrosurgical Devices," issued Dec. 27, 2016, the disclosure of which is incorporated by reference herein, in its entirety.

Some electrosurgical instruments include an end effector with at least one compliant feature. Examples of such instruments are described in U.S. Pat. No. 9,149,325, entitled "End Effector with Compliant Clamping Jaw," issued Oct. 6, 2015, the disclosure of which is incorporated by reference herein, in its entirety; and U.S. Pat. No. 9,877,782, entitled "Electrosurgical Instrument End Effector with Compliant Electrode," issued Jan. 30, 2018, the disclosure of which is incorporated by reference herein, in its entirety.

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
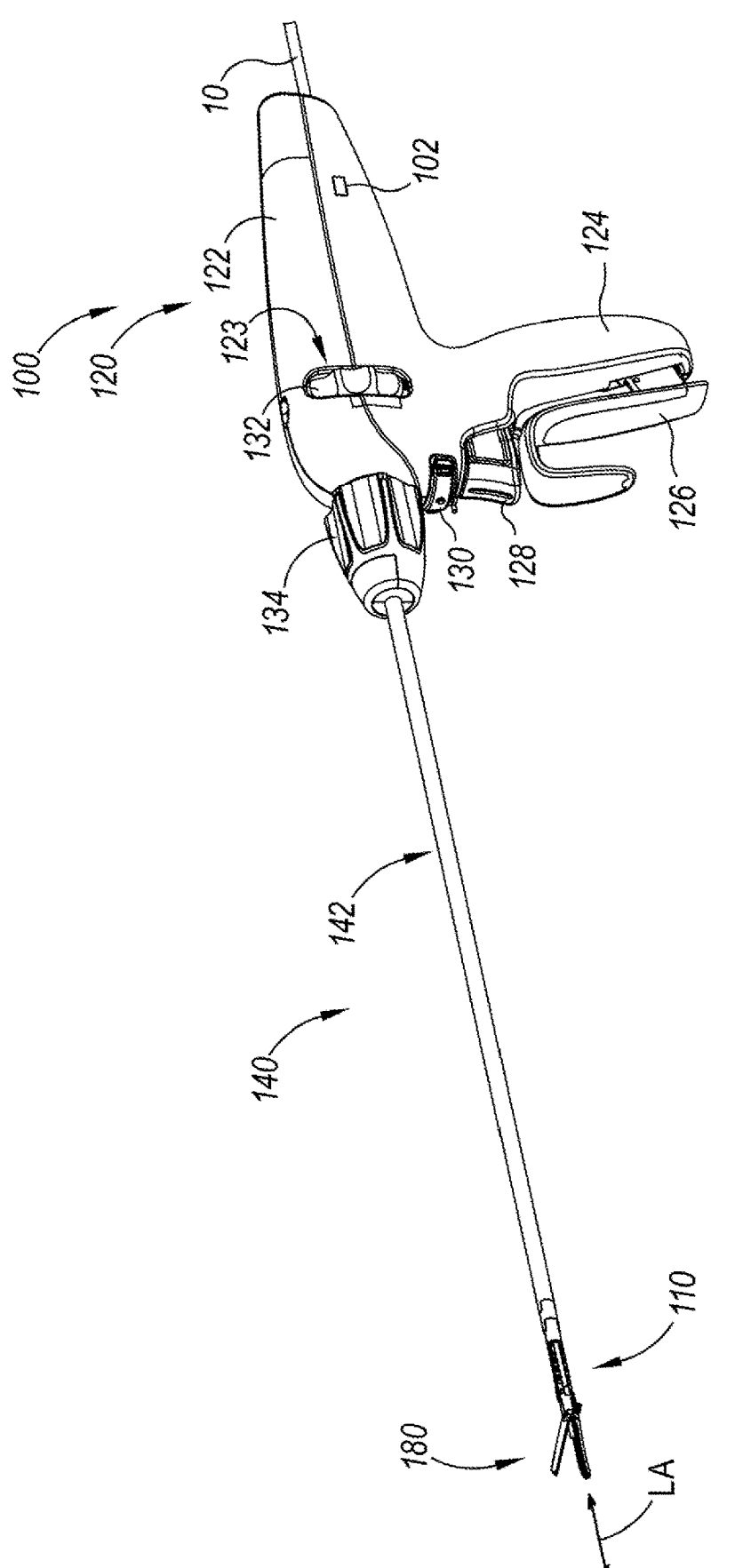
FIG. 1 depicts a perspective view of an exemplary electrosurgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. EXAMPLE OF ELECTROSURGICAL INSTRUMENT

FIGS. 1-3C show an exemplary electrosurgical instrument (100). As best seen in FIG. 1, electrosurgical instrument (100) includes a handle assembly (120), a shaft assembly (140), an articulation assembly (110), and an end effector (180). As will be described in greater detail below, end effector (180) of electrosurgical instrument (100) is operable to grasp, cut, and seal or weld tissue (e.g., a blood vessel, etc.). In this example, end effector (180) is configured to seal or weld tissue by applying bipolar radio frequency (RF) energy to tissue. However, it should be understood electrosurgical instrument (100) may be configured to seal or weld tissue through any other suitable means that would be apparent to one skilled in the art in view of the teachings herein. For example, electrosurgical instrument (100) may be configured to seal or weld tissue via an ultrasonic blade, staples, etc. In the present example, electrosurgical instrument (100) is electrically coupled to a power source (not shown) via power cable (10).

The power source may be configured to provide all or some of the electrical power requirements for use of electrosurgical instrument (100). Any suitable power source may be used as would be apparent to one skilled in the art in view of the teachings herein. By way of example only, the power source may comprise a GEN04 or GEN11 sold by Ethicon Endo-Surgery, Inc. of Cincinnati, Ohio. In addition, or in the alternative, the power source may be constructed in accordance with at least some of the teachings of U.S. Pat. No. 8,986,302, entitled "Surgical Generator for Ultrasonic and Electrosurgical Devices," issued Mar. 24, 2015, the disclosure of which is incorporated by reference herein, in its entirety. While in the current example, electrosurgical instrument (100) is coupled to a power source via power cable (10), electrosurgical instrument (100) may contain an internal power source or plurality of power sources, such as a battery and/or supercapacitors, to electrically power electrosurgical instrument (100). Of course, any suitable combination of power sources may be utilized to power electrosurgical instrument (100) as would be apparent to one skilled in the art in view of the teaching herein.

Handle assembly (120) is configured to be grasped by an operator with one hand, such that an operator may control and manipulate electrosurgical instrument (100) with a single hand. Shaft assembly (140) extends distally from handle assembly (120) and connects to articulation assembly (110). Articulation assembly (110) is also connected to a proximal end of end effector (180). As will be described in greater detail below, components of handle assembly (120) are configured to control end effector (180) such that an operator may grasp, cut, and seal or weld tissue. Articulation assembly (110) is configured to deflect end effector (180) from the longitudinal axis (LA) defined by shaft assembly (140).

Handle assembly (120) includes a control unit (102) housed within a body (122), a pistol grip (124), a jaw closure trigger (126), a knife trigger (128), an activation button (130), an articulation control (132), and a knob (134). As will be described in greater detail below, jaw closure trigger (126) may be pivoted toward and away from pistol grip (124) and/or body (122) to open and close jaws (182, 184)

of end effector (180) to grasp tissue. Additionally, knife trigger (128) may be pivoted toward and away from pistol grip (124) and/or body (122) to actuate a knife member (176) within the confines of jaws (182, 184) to cut tissue captured between jaws (182, 184). Further, activation button (130) may be pressed to apply radio frequency (RF) energy to tissue via electrode surfaces (194, 196) of jaws (182, 184), respectively.

Body (122) of handle assembly (120) defines an opening (123) in which a portion of articulation control (132) protrudes from. Articulation control (132) is rotatably disposed within body (122) such that an operator may rotate the portion of articulation control (132) protruding from opening (123) to rotate the portion of articulation control (132) located within body (122). Rotation of articulation control (132) relative to body (122) is configured to bend articulation section (110) in order to drive deflection of end effector (180) from the longitudinal axis (LA) defined by shaft assembly (140). Articulation control (132) and articulation section (110) may include any suitable features to drive deflection of end effector (180) from the longitudinal axis (LA) defined by shaft assembly (140) as would be apparent to one skilled in the art in view of the teachings herein.

Knob (134) is rotatably disposed on the distal end of body (122) and configured to rotate end effector (180), articulation assembly (110), and shaft assembly (140) about the longitudinal axis (LA) of shaft assembly (140) relative to handle assembly (120). While in the current example, end effector (180), articulation assembly (110), and shaft assembly (140) are rotated by knob (134), knob (134) may be configured to rotate end effector (180) and articulation assembly (110) relative to selected portions of shaft assembly (140). Knob (134) may include any suitable features to rotate end effector (180), articulation assembly (110), and shaft assembly (140) as would be apparent to one skilled in the art in view of the teachings herein.

Figure 3:
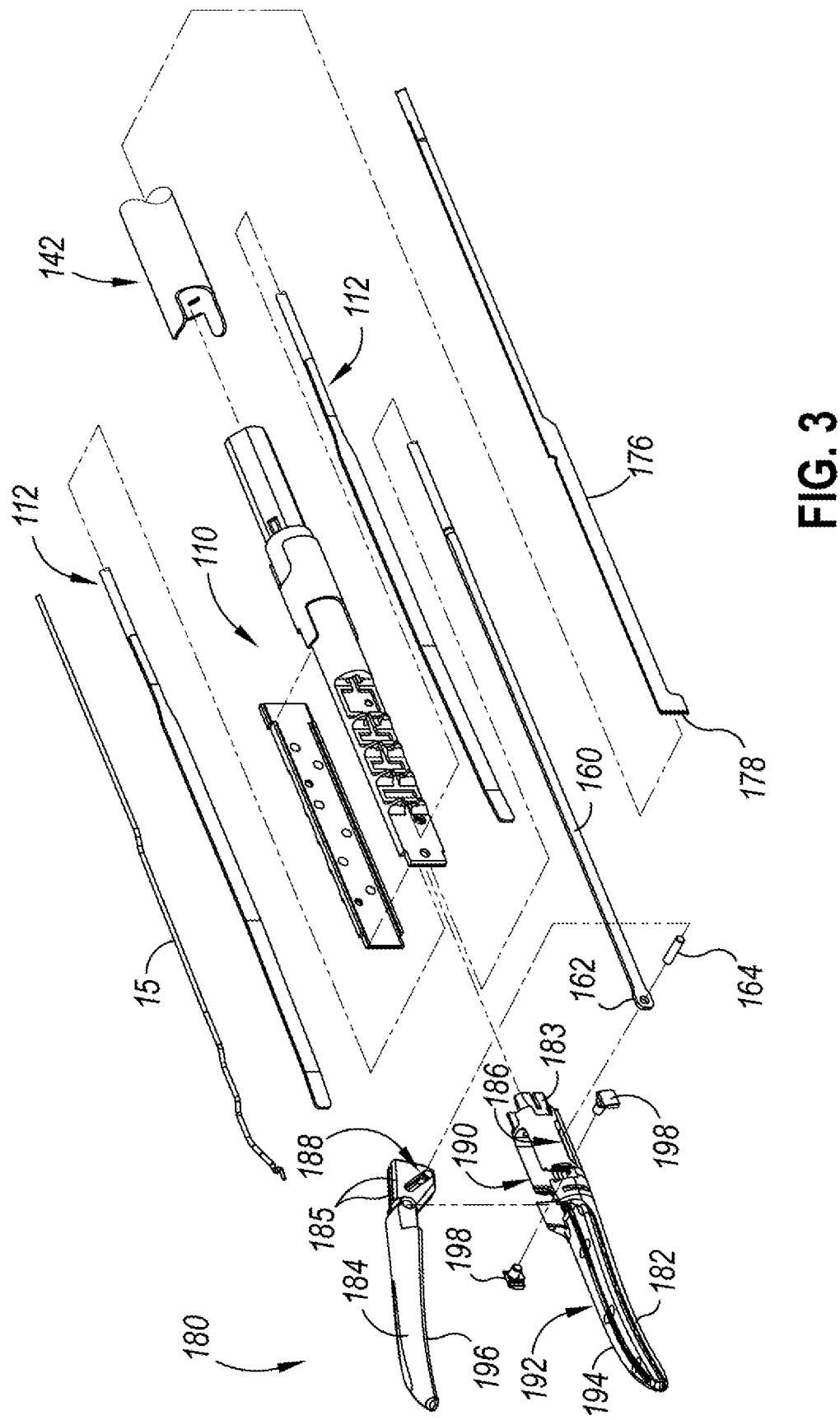
FIG. 3 depicts an exploded view of the articulation assembly and end effector of FIG. 2.

Shaft assembly (140) includes distal portion (142) extending distally from handle assembly (120), and a proximal portion (144) (see FIGS. 4A-4B) housed within the confines of body (122) of handle assembly (120). As best shown in FIG. 3, shaft assembly (140) houses a jaw closure connector (160) that couples jaw closure trigger (126) with end effector (180). Additionally, shaft assembly (140) houses a portion of knife member extending between distal cutting edge (178) and knife trigger (128). Shaft assembly (140) also houses actuating members (112) that couple articulation assembly (110) with articulation control (132); as well as an electrical connecter (15) that operatively couples electrode surfaces (194, 196) with activation button (130). As will be described in greater detail below, jaw closure connector (160) is configured to translate relative to shaft assembly (140) to open and close jaws (182, 184) of end effector (180); while knife member (176) is coupled to knife trigger (128) of handle assembly (120) to translate distal cutting edge (178) within the confines of end effector (180); and activation button (130) is configured to activate electrode surface (194, 196).

Figure 2:
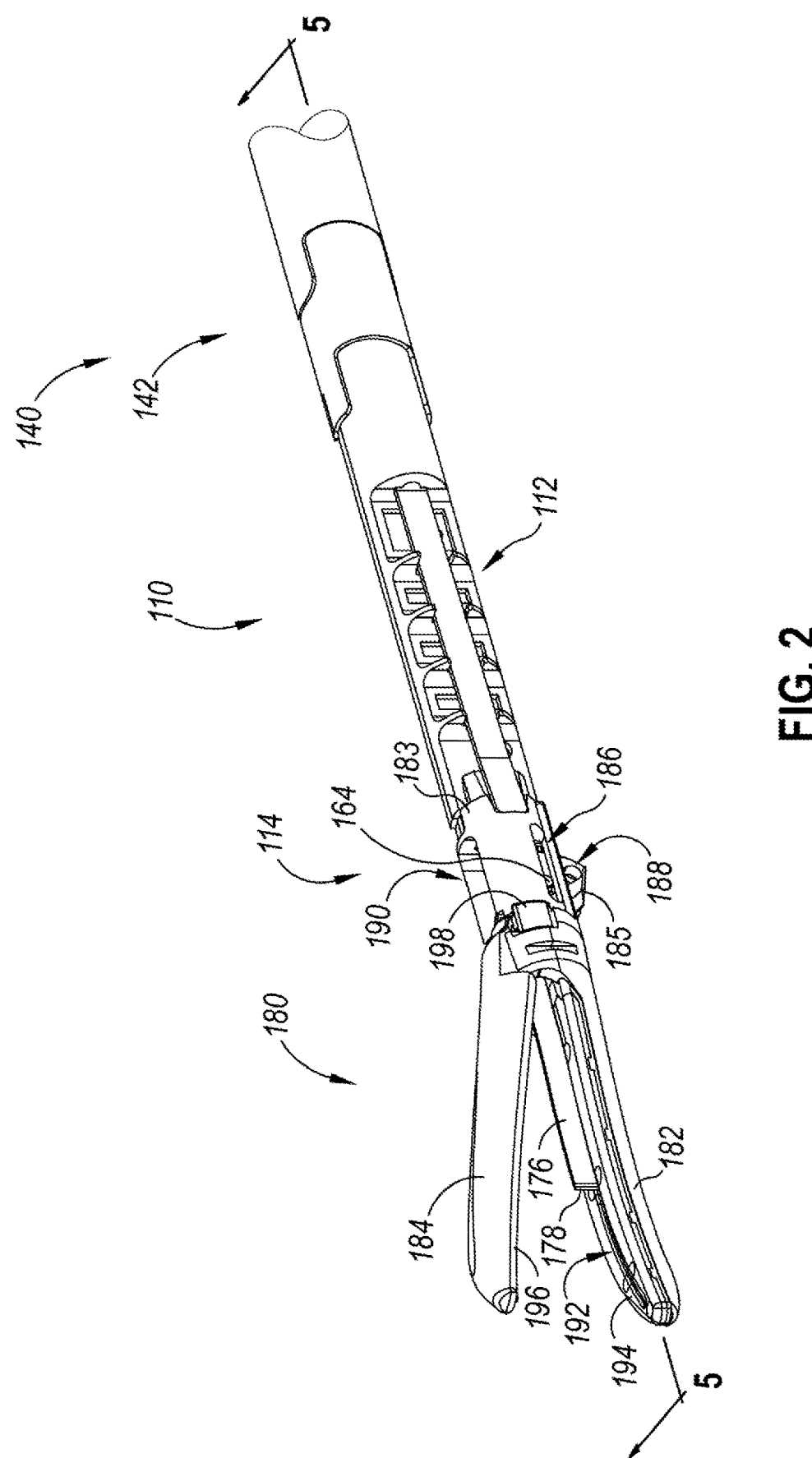
FIG. 2 depicts a perspective view of an exemplary articulation assembly and end effector of the electrosurgical instrument of FIG. 1.
Figure 5A:
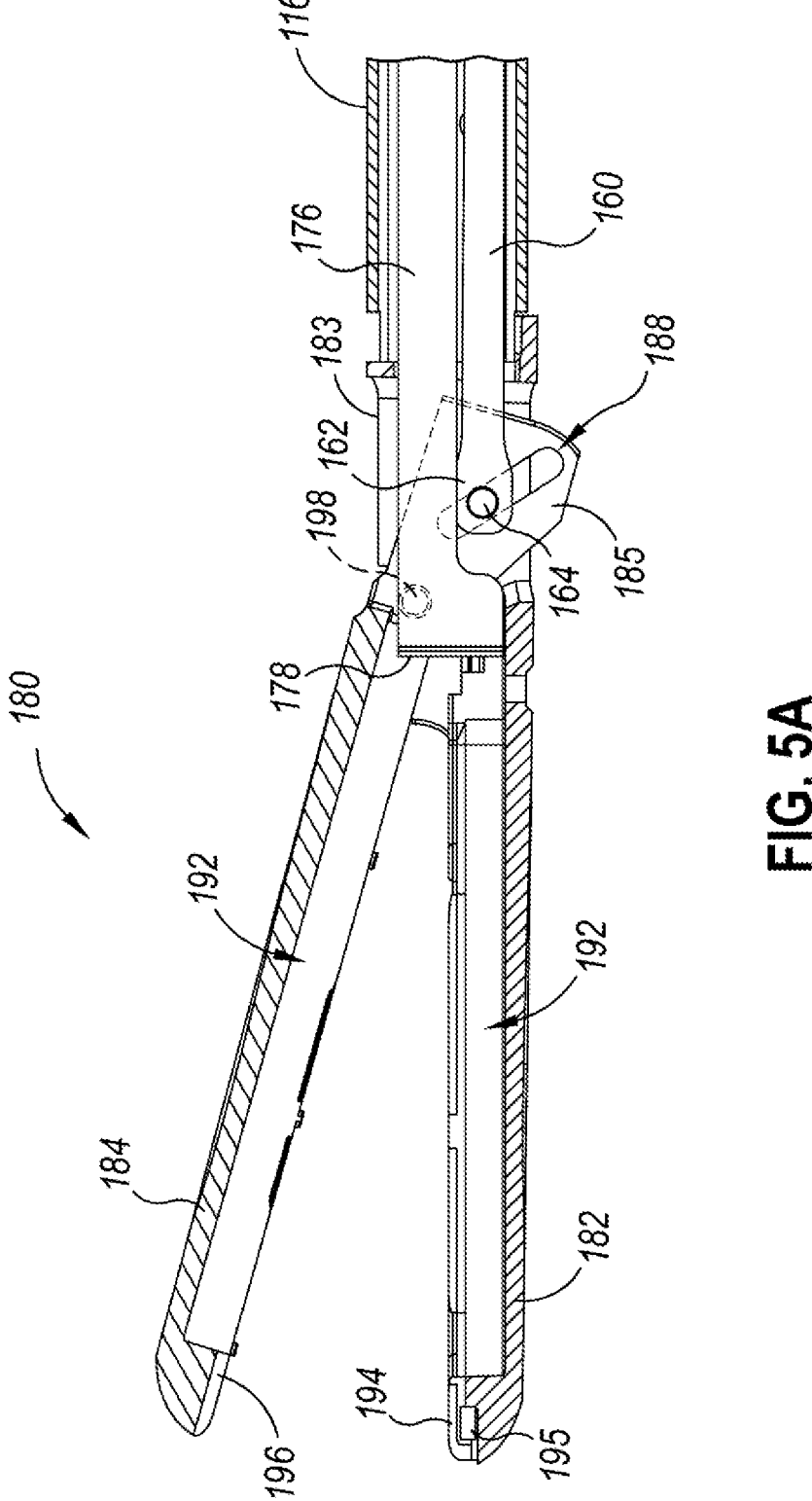
FIG. 5A depicts a cross-sectional side view of the end effector of FIG. 2, where the end effector is in the open and unfired state, taken along line 5-5 of FIG. 2.
Figure 5B:
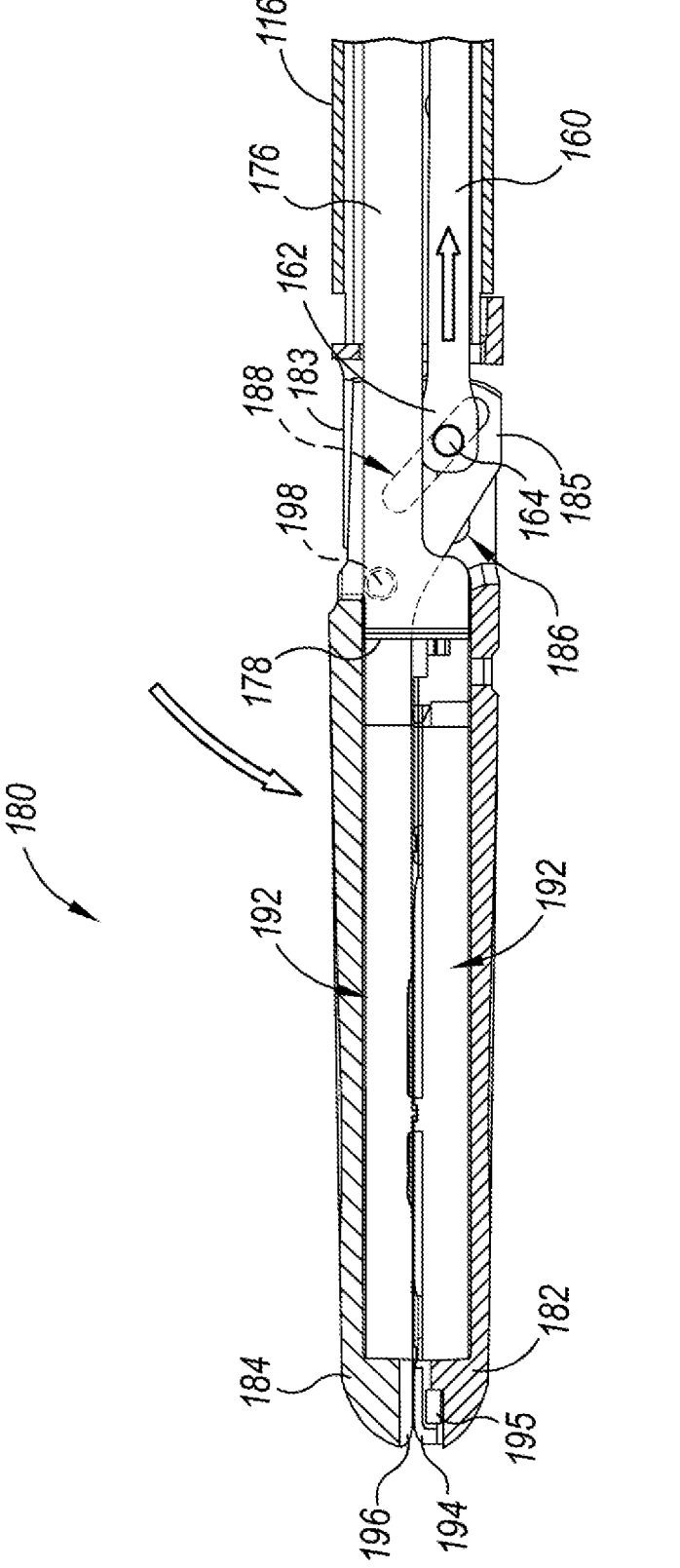
FIG. 5B depicts a cross-sectional side view of the end effector of FIG. 2, where the end effector is in the closed and unfired state, taken along line 5-5 of FIG. 2.
Figure 5C:
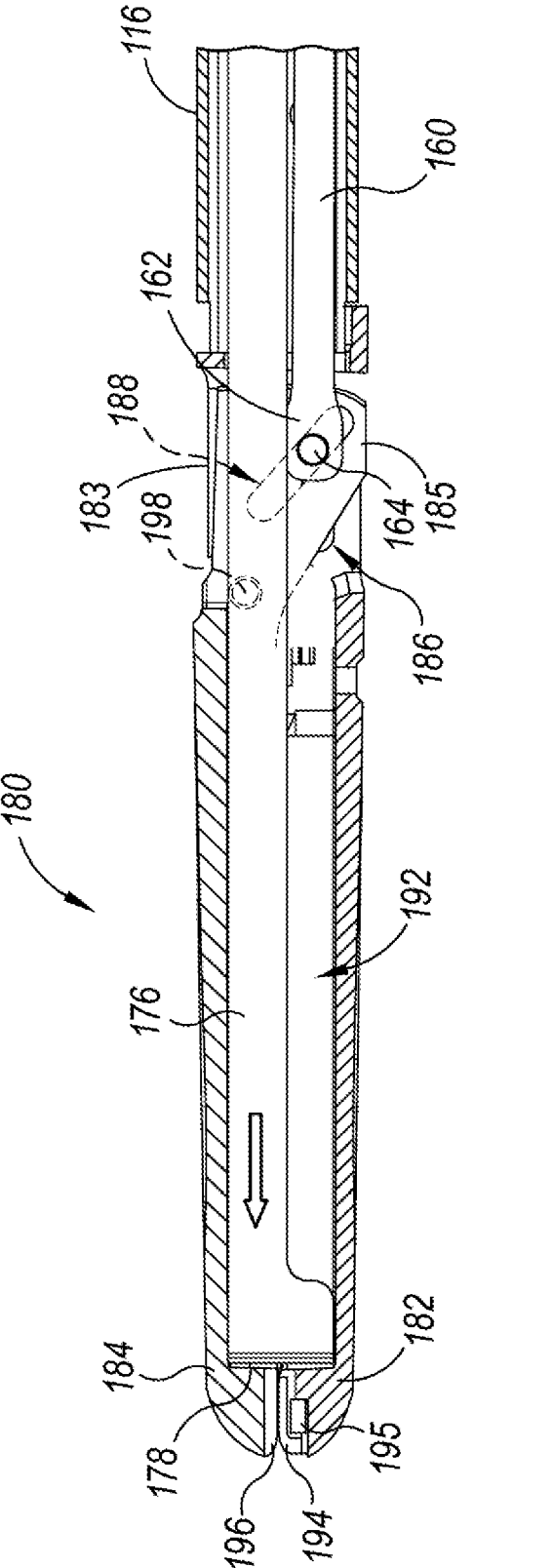
FIG. 5C depicts a cross-sectional side view of the end effector of FIG. 2, where the end effector is in the closed and fired state, taken along line 5-5 of FIG. 2.

As best seen in FIGS. 2-3, end effector (180) includes lower jaw (182) pivotally coupled with upper jaw (184) via pivot couplings (198). Lower jaw (182) includes a proximal body (183) defining a slot (186), while upper jaw (184) includes proximal arms (185) defining a slot (188). Lower jaw (182) also defines a central channel (190) that is configured to receive proximal arms (185) of upper jaw (184), portions of knife member (176), jaw closure connecter (160), and pin (164). Slots (186, 188) each slidably receive pin (164), which is attached to a distal coupling portion (162) of jaw closure connector (160). Additionally, as best seen in FIGS. 5A-5C, lower jaw (182) includes a force sensor (195) located at a distal tip of lower jaw (182). Force sensor (195) may be in communication with control unit (102). Force sensor (195) may be configured to measure the closure force generated by pivoting jaws (182, 184) into a closed configuration in accordance with the description herein. Additionally, force sensor (195) may communicate this data to control unit (102). Any suitable components may be used for force sensor (195) as would be apparent to one skilled in art in view of the teachings herein. For example, force sensor (195) may take the form of a strain gauge.

While in the current example, a force sensor (195) is incorporated into instrument (100) and is in communication with control unit (102), any other suitable sensors or feedback mechanisms may be additionally or alternatively incorporated into instrument (100) while in communication with control unit (102) as would be apparent to one skilled in the art in view of the teachings herein. For instance, an articulation sensor or feedback mechanism may be incorporated into instrument (100), where the articulation sensor communicates signals to control unit (102) indicative of the degree end effector (180) is deflected from the longitudinal axis (LA) by articulation control (132) and articulation section (110).

As will be described in greater detail below, jaw closure connector (160) is operable to translate within central channel (190) of lower jaw (182). Translation of jaw closure connector (160) drives pin (164). As will also be described in greater detail below, with pin (164) being located within both slots (186, 188), and with slots (186, 188) being angled relative to each other, pin (164) cams against proximal arms (185) to pivot upper jaw (184) toward and away from lower jaw (182) about pivot couplings (198). Therefore, upper jaw (184) is configured to pivot toward and away from lower jaw (182) about pivot couplings (198) to grasp tissue.

The term "pivot" does not necessarily require rotation about a fixed axis and may include rotation about an axis that moves relative to end effector (180). Therefore, the axis at which upper jaw (184) pivots about lower jaw (182) may translate relative to both upper jaw (184) and lower jaw (182). Any suitable translation of the pivot axis may be used as would be apparent to one skilled in the art in view of the teachings herein.

Lower jaw (182) and upper jaw (184) also define a knife pathway (192). Knife pathway (192) is configured to slidably receive knife member (176), such that knife member (176) may be retracted (as shown in FIGS. 5A-5B), and advanced (as shown in FIG. 5C), to cut tissue captured between jaws (182, 184). Lower jaw (182) and upper jaw (184) each comprise a respective electrode surface (194, 196). The power source may provide RF energy to electrode surfaces (194, 196) via electrical coupling (15) that extends through handle assembly (120), shaft assembly (140), articulation assembly (110), and electrically couples with one or both of electrode surfaces (194, 196). Electrical coupling (15) may selectively activate electrode surfaces (194, 196) in response to an operator pressing activation button (130). In some instances, control unit (102) may couple electrical coupling (15) with activation button (130), such that control unit (102) activates electrode surfaces (194, 196) in response to operator pressing activation button (130). Control unit (102) may have any suitable components in order to perform suitable functions as would be apparent to one skilled in the art in view of the teachings herein. For instance, control unit (102) may have a processor, memory unit, suitable circuitry, etc.

FIGS. 4A-5C show an exemplary use of instrument (100) for end effector (180) to grasp, cut, and seal/weld tissue. As described above, and as shown between FIGS. 4A-4B and 5A-5B, jaw closure trigger (126) may be pivoted toward and away from pistol grip (124) and/or body (122) to open and close jaws (182, 184) of end effector (180) to grasp tissue. In particular, as will be described in greater detail below, pivoting jaw closure trigger (126) toward pistol grip (124) may proximally actuate jaw closure connector (160) and pin (164), which in turn cams against slots (188) of proximal arms (185) of upper jaw (184), thereby rotating upper jaw (184) about pivot couplings (198) toward lower jaw (182) such that jaws (182, 184) achieve a closed configuration.

Handle assembly (120) further includes a yoke assembly (200) that is slidably coupled along proximal portion (144) of shaft assembly (140). Yoke assembly (200) is operatively coupled with jaw closure connector (160) such that translation of yoke assembly (200) relative to proximal portion (144) of shaft assembly (140) translates jaw closure connector (160) relative to shaft assembly (140).

Figure 4A:
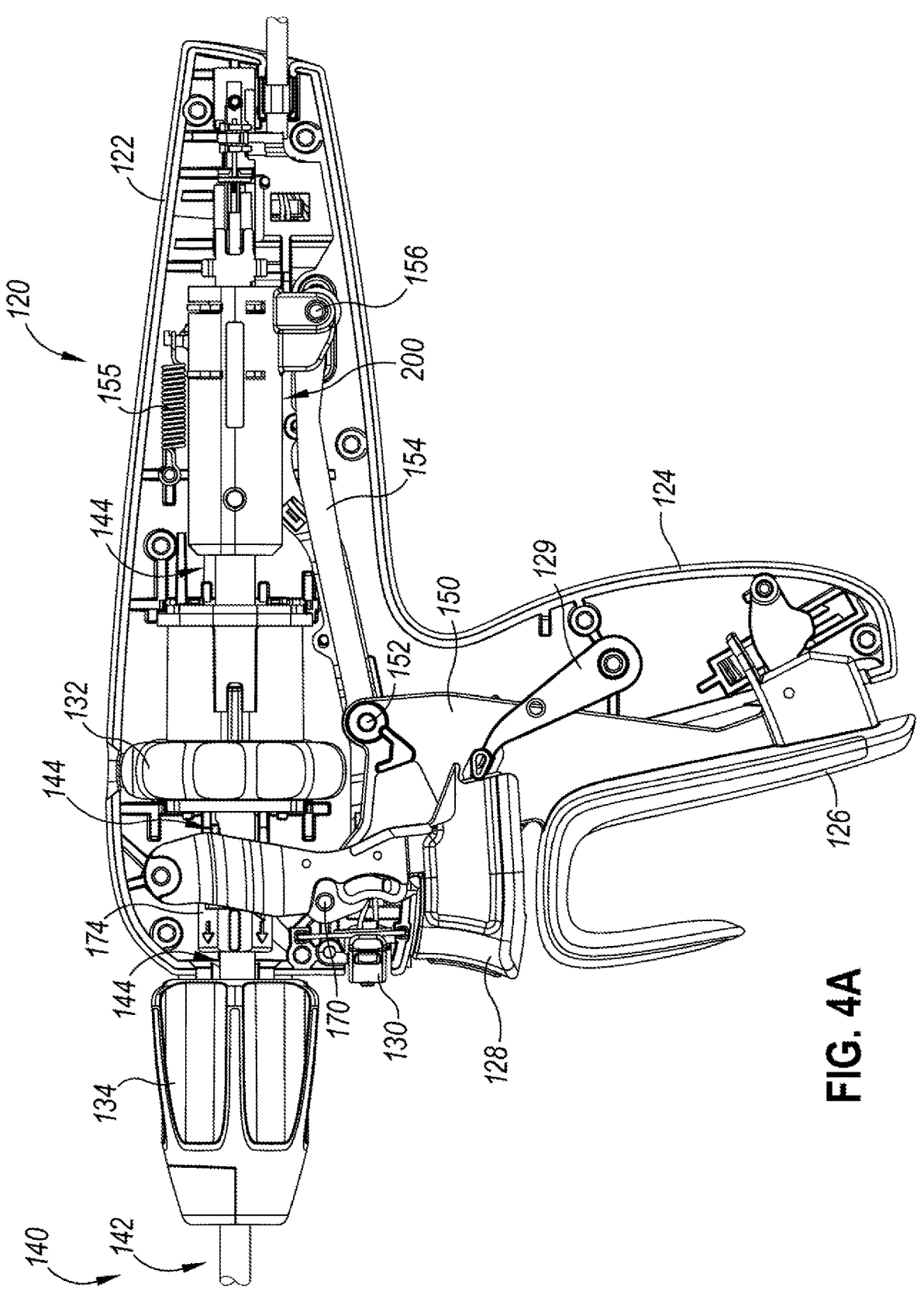
FIG. 4A depicts a side elevational view of a handle assembly of the electrosurgical instrument of FIG. 1, where the end effector is in an open and unfired state, where a portion of the handle assembly is omitted for purposes of clarity.
Figure 4B:
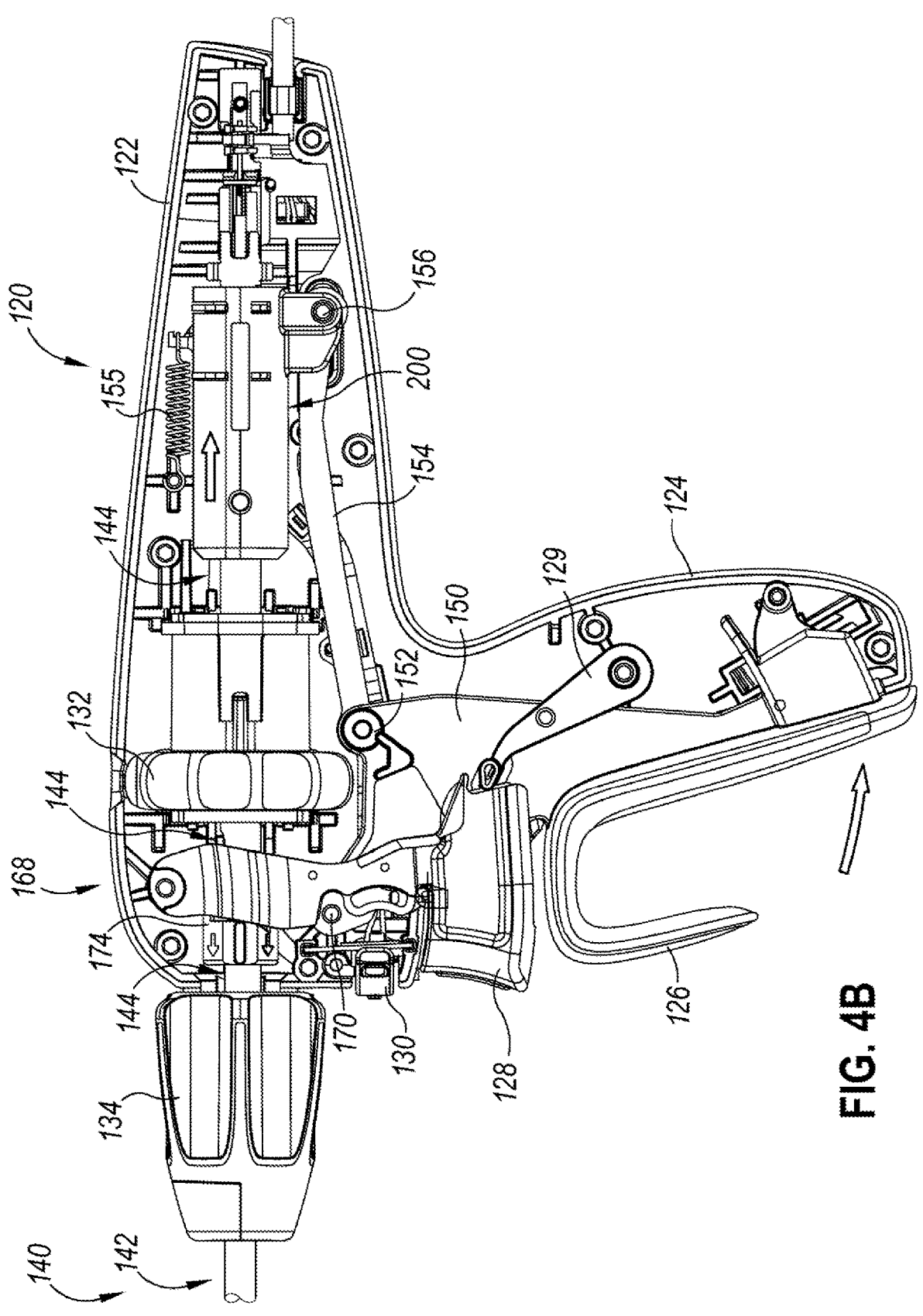
FIG. 4B depicts a side elevational view of the handle assembly of FIG. 4A, where the end effector is in a closed and unfired state, where a portion of the handle assembly is omitted for purposes of clarity.
Figure 4C:
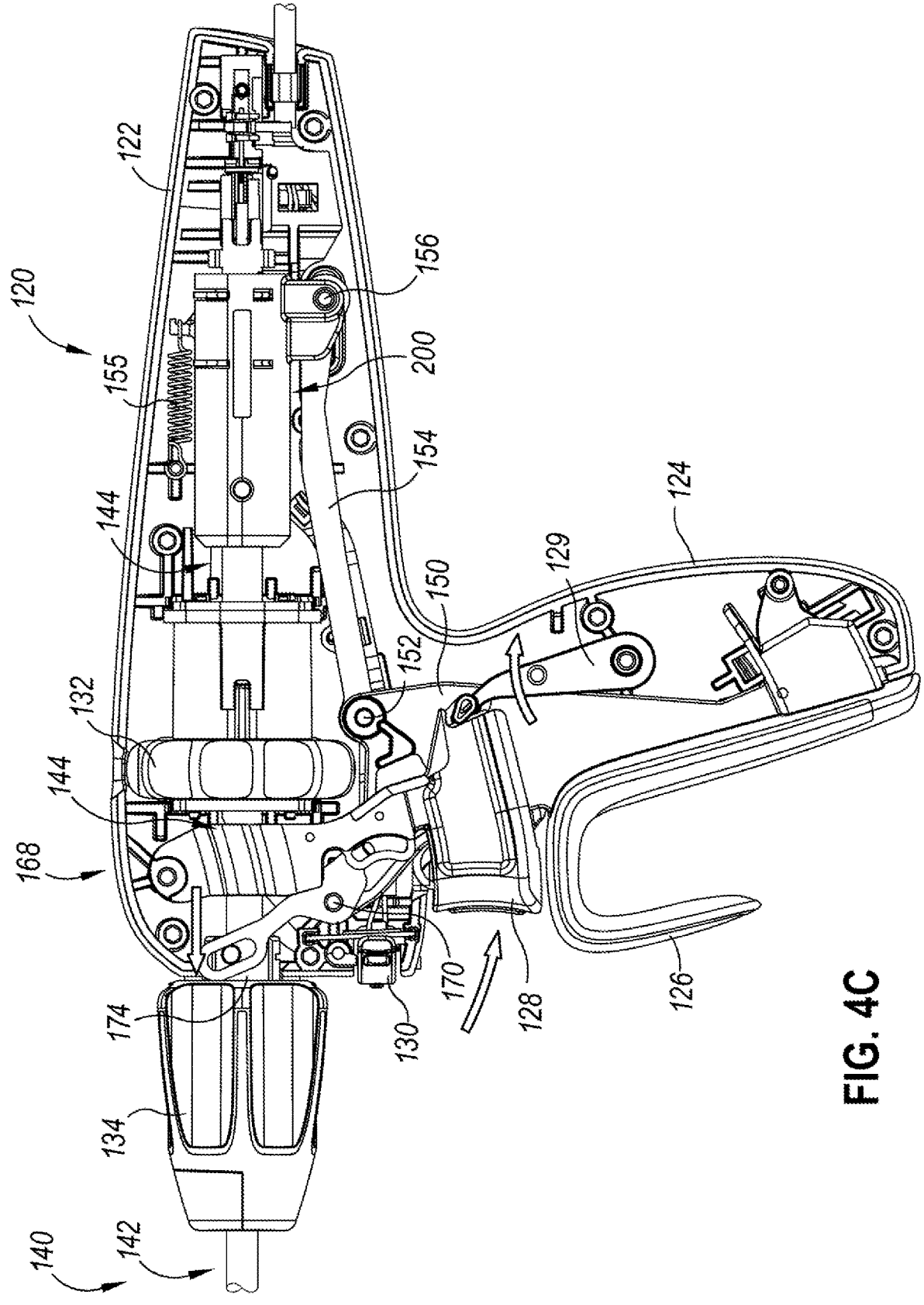
FIG. 4C depicts a side elevational view of the handle assembly of FIG. 4A, where the end effector is in a closed and fired state, where a portion of the handle assembly is omitted for purposes of clarity.

As best seen in FIGS. 4A-4C, yoke assembly (200) is coupled to a body (150) of jaw closure trigger (126) via a link (154). Link (154) is pivotally coupled with yoke assembly (200) via pin (156); while link (154) is also pivotally coupled with body (150) of jaw closure trigger (126) via pin (152). Additionally, jaw closure trigger (126) is pivotally coupled with body (122) of handle assembly (120) via pin (170). Therefore, as shown between FIGS. 4A-4B, an operator may pull jaw closure trigger (126) toward pistol grip (124), thereby rotating jaw closure trigger (126) about pin (170). Rotation of jaw closure trigger (126) leads to rotation of link (154) about both pins (152, 156), which in turn drives yoke assembly (200) in the proximal direction along proximal portion (144) of shaft assembly (140).

As described above, jaw closure connector (160) extends within shaft assembly (140), articulation section (110), and central channel (190) of lower jaw (182). As also mentioned above, jaw closure connector (160) is attached to pin (164). Therefore, as seen between FIGS. 5A-5B, proximal translation of yoke assembly (200) leads to proximal translation of pin (164), which in turn cams against slots (188) of proximal arms (185) of upper jaw (184), thereby rotating upper jaw (184) about pivot couplings (198) toward lower jaw (182) such that jaws (182, 184) achieve a closed configuration.

As best seen in FIGS. 4A-4C, yoke assembly (200) is also coupled with a bias spring (155). Bias spring (155) is also coupled to a portion of body (122), such that bias spring (155) biases yoke assembly (200) to the position shown in FIG. 4A (associated with the open configuration of end effector (180) as shown in FIG. 5A). Therefore, if an operator releases jaw closure trigger (126), bias spring (155) will translate yoke assembly (200) to the position shown in FIG. 4A, thereby opening jaws (182, 184) of end effector (180).

As described above, and as shown between FIGS. 4B-4C and 5B-5C, knife trigger (128) may be pivoted toward and away from body (122) and/or pistol grip (124) to actuate knife member (176) within knife pathway (192) of jaws (182, 184) to cut tissue captured between jaws (182, 184). In particular, handle assembly (120) further includes a knife coupling body (174) that is slidably coupled along proximal portion (144) of shaft assembly (140). Knife coupling body (174) is coupled with knife member (176) such that translation of knife coupling body (174) relative to proximal portion (144) of shaft assembly (140) translates knife member (176) relative to shaft assembly (140).

As best seen in FIGS. 4B-4C and 5B-5C, knife coupling body (174) is coupled a knife actuation assembly (168) such that as knife trigger (128) pivots toward body (122) and/or pistol grip (124), knife actuation assembly (168) drives knife coupling body (174) distally, thereby driving knife member (176) distally within knife pathway (192). Because knife coupling body (174) is coupled to knife member (176), knife member (176) translates distally within shaft assembly (140), articulation section (110), and within knife pathway (192) of end effector (180), as best shown between FIGS. 5B-5C. Knife member (176) includes distal cutting edge (178) that is configured to sever tissue captured between jaws (182, 184). Therefore, pivoting knife trigger (128) causes knife member (176) to actuate within knife pathway (192) of end effector (180) to sever tissue captured between jaws (182, 184).

Knife trigger (128) is biased to the positions seen in FIGS. 4A-4B (associated with the knife member (176) in the retracted position) by a bias arm (129). Bias arm (129) may include any suitable biasing mechanism as would be apparent to one having ordinary skill in the art in view of the teachings herein. For instance, bias arm (129) may include a torsion spring. Therefore, if an operator releases knife trigger (128), bias arm (129) returns knife trigger (128) to the position shown in FIGS. 4A-4B, thereby translating knife member (176) toward the retracted position.

With distal cutting edge (178) of knife member (176) actuated to the advance position (position shown in FIG. 5C), an operator may press activation button (130) to selectively activate electrode surfaces (194, 196) of jaws (182, 184) to weld/seal severed tissue that is captured between jaws (182, 184). It should be understood that the operator may also press activation button (130) to selectively activate electrode surfaces (194, 196) of jaws (182, 184) at any suitable time during exemplary use. Therefore, the operator may also press activation button (130) while knife member (176) is retracted as shown in FIGS. 3A-3B. Next, the operator may release jaw closure trigger (128) such that jaws (182, 184) pivot into the opened configuration, releasing tissue.

II. EXAMPLES OF OPTICAL SENSING DEVICES FOR ELECTROSURGICAL INSTRUMENT

As mentioned above, end effector (180) is configured to grasp, sever, and weld/seal tissue. In particular, jaw (184) may pivot relative to jaw (182) in order to grasp tissue, while knife member (176) is configured to actuate within jaws (182, 184) in order to sever tissue that is grasped between jaws (182, 184). Electrode surfaces (194, 196) may be activated while jaws (182, 184) grasp tissue in order to weld/seal tissue captured between jaws (182, 184). In some instances, it may be desirable to equip end effector (180) with one or more optical sensors for detecting tissue before, during, and/or after grasping, severing, and/or welding/ sealing the tissue. Such optical sensors may be utilized to determine a status of the tissue, such as a property of the tissue and/or a position of the tissue relative to end effector (180), for example. It may also be desirable for such optical sensors to be compact while also being capable of enduring heat, close proximity to RF energy delivery, and high clamping forces, without interfering with the operation of knife member (176) and/or electrode surfaces (194, 196). For example, it may be desirable for such optical sensors to fit within an end effector (180) having a length of approximately 5 mm. Each of the electrosurgical instruments described below provides one or more of these functionalities.

A. Exemplary Electrosurgical Instrument with Optical Sensing Lightboxes

Figure 6:
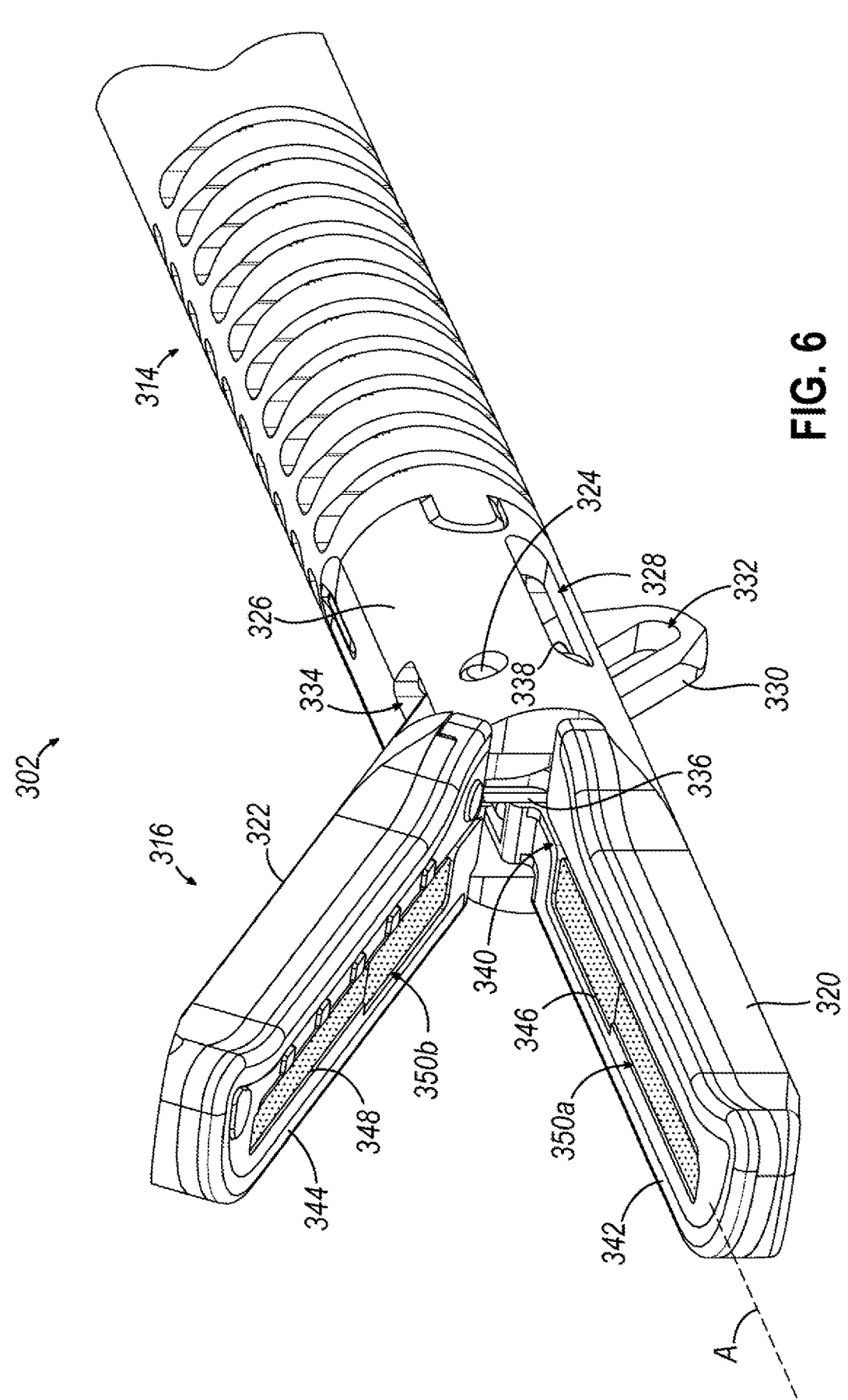
FIG. 6 depicts a perspective view of a distal portion of another exemplary electrosurgical instrument with an end effector having upper and lower optical sensing lightboxes positioned on respective jaws thereof for detecting tissue between the jaws.
Figure 7:
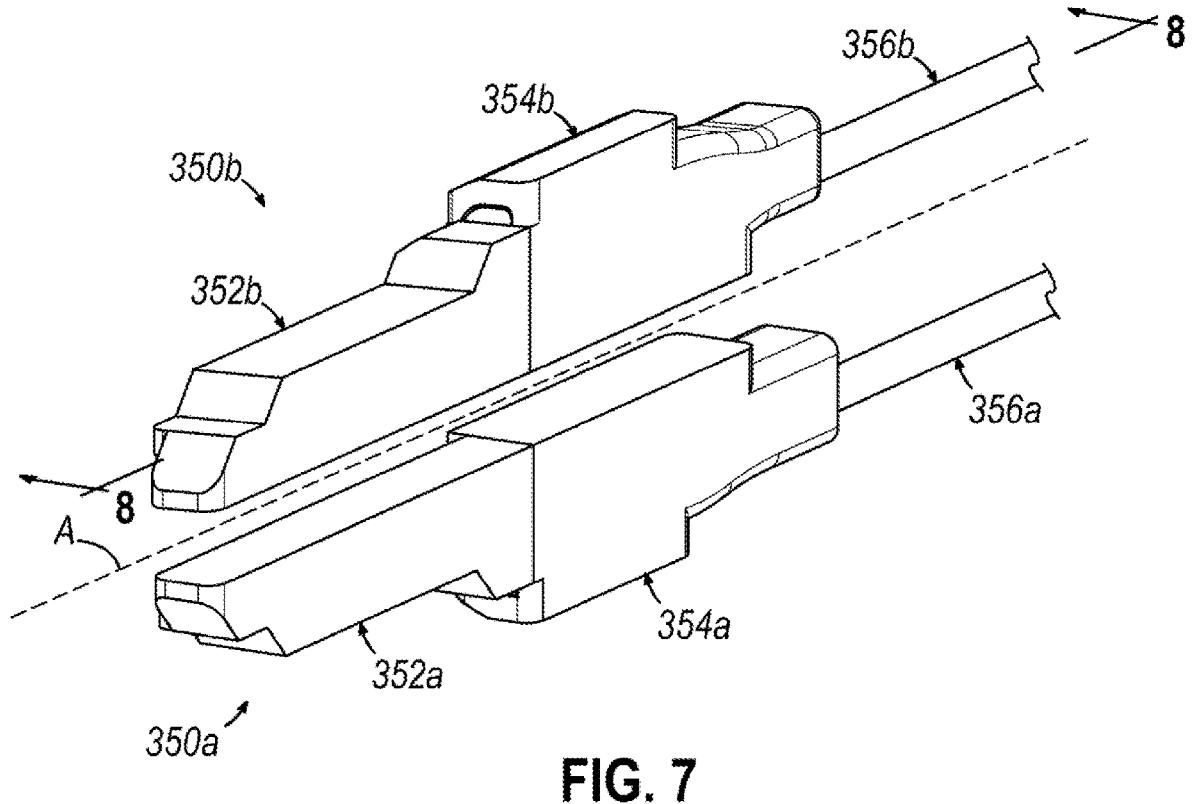
FIG. 7 depicts a perspective view of the lightboxes of FIG. 6, showing the lightboxes coupled to respective optical fiber bundles.
Figure 8:
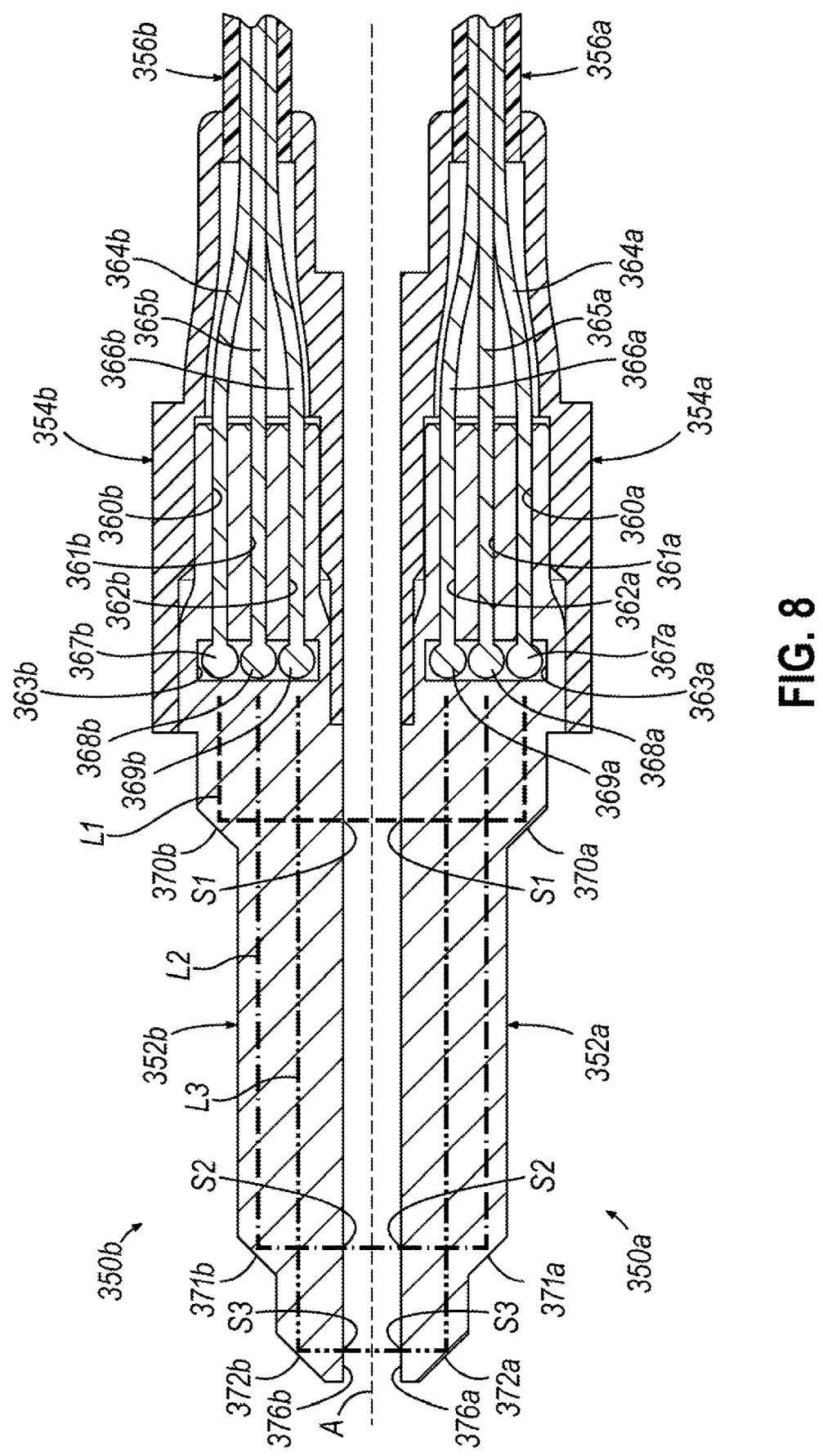
FIG. 8 depicts a cross-sectional side view of the lightboxes of FIG. 6, taken along section line 8-8 in FIG. 7, showing light beams emitted from respective optical fiber bundles and reflected by corresponding light reflection elements of the lightbox.

FIGS. 6-8 show an exemplary electrosurgical instrument (302) having optical sensing capabilities. Electrosurgical instrument (302) is similar to electrosurgical instrument (100) described above except as otherwise described below. In this regard, electrosurgical instrument (302) of this example includes a handle assembly (not shown), such as handle assembly (120), a shaft assembly (not shown), such as shaft assembly (140), an articulation assembly (314), and an end effector (316) that is operable to grasp, cut, and seal or weld tissue (e.g., a blood vessel, etc.) by applying bipolar RF energy provided by a generator (not shown) to tissue.

In the example shown, end effector (316) includes a lower jaw (320) pivotally coupled with an upper jaw (322) via pivot couplings (324). Lower jaw (320) includes a proximal body (326) defining a slot (328), while upper jaw (322) includes proximal arms (330) defining a slot (332). Lower jaw (320) also defines a central channel (334) that is configured to receive proximal arms (330) of upper jaw (322), portions of a knife member (336), a jaw closure connecter (not shown), such as jaw closure connector (160), and a pin (338). Slots (328, 332) each slidably receive pin (338), which is attached to a distal coupling portion (not shown) of the jaw closure connector. Lower jaw (320) and upper jaw (322) also define a knife pathway (340) configured to slidably receive knife member (336), such that knife member (336) may be retracted and advanced to cut tissue captured between jaws (320, 322). Lower jaw (320) and upper jaw (322) each comprise a respective electrode surface (342, 344) electrically coupled to a power source (not shown) for providing RF energy to electrode surfaces (342, 344).

In the example shown, lower jaw (320) and upper jaw (322) also each comprise respective recess (346, 348), each of which opens toward the corresponding electrode surface (342, 344). In this regard, end effector (316) of the present version further includes a pair of optical sensing devices in the form of a lower lightbox (350a) received within recess (346) of lower jaw (320) and an upper lightbox (350b) received within recess (348) of upper jaw (322). Each lightbox (350a, 350b) is capable of transmitting light and/or receiving light in a predetermined guided manner, as described in greater detail below. As shown, recesses (346, 348) are each sized to permit the respective lightboxes (350a, 350b) to be positioned adjacent to knife pathway (340) to thereby prevent lightboxes (350a, 350b) from interfering with advancement and retraction of knife member (336). Each lightbox (350a, 350b) may be fixedly secured to the respective jaw (320, 322) within the corresponding recess (346, 348) in any suitable manner. For example, each lightbox (350a, 350b) may include one or more coupling features such as ledges and/or press pins (not shown) configured to frictionally engage respective coupling features of the corresponding recess (346, 348). In some versions, adhesive may be applied between each lightbox (350a, 350b) and the corresponding recess (346, 348) to assist with securing lightboxes (350a, 350b) to the respective jaws (320, 322). To that end, the coupling features of each lightbox (350a, 350b) may include one or more adhesive reservoirs (not shown).

As best shown in FIGS. 7-8, each lightbox (350a, 350b) includes a housing in the form of a distal body (352a, 352b) fixedly coupled to a corresponding proximal cover (354a,

354b). Each body (352a, 352b) may comprise a material having an opacity configured to allow the passage of light therethrough, such as a translucent and/or transparent material. In any event, each lightbox (350a, 350b) is configured to transmit light to and/or receive light from a corresponding illuminating and/or light receiving element in the form of an optical fiber bundle (356a, 356b), which is operatively coupled to a proximal light source and/or proximal light reader (not shown).

In this regard, each body (352a, 352b) includes a plurality of optical fiber guide ports (360a, 360b, 361a, 361b, 362a, 362b) extending distally from a proximal end thereof for receiving respective portions of the corresponding optical fiber bundle (356a, 356b). More particularly, each body (352a, 352b) of the present version includes a transversely outer optical fiber guide port (360a, 360b), a transversely intermediate optical fiber guide port (361a, 361b), and a transversely inner optical fiber guide port (362a, 362b), which collectively terminate at a corresponding optical fiber anchoring chamber (363a, 363b).

Each optical fiber guide port (360a, 360b, 361a, 361b, 362a, 362b) is configured to receive a respective optical fiber (364a, 364b, 365a, 365b, 366a, 366b) of the corresponding optical fiber bundle (356a, 356b), while each optical fiber anchoring chamber (363a, 363b) is configured to receive bulbous distal lenses (367a, 367b, 368a, 368b, 369a, 369b) of the optical fibers (364a, 364b, 365a, 365b, 366a, 366b) of the corresponding optical fiber bundle (356a, 356b) to thereby anchor or otherwise secure optical fiber bundles (356a, 356b) to lightboxes (350a, 350b), respectively, in predetermined positions and/or orientations relative to lightboxes (350a, 350b). For example, at least a distal portion of each optical fiber (364a, 364b, 365a, 365b, 366a, 366b) may be generally parallel to a longitudinal axis of the respective body (352a, 352b) (which may itself be parallel to a longitudinal axis (A) of end effector (316), for example) such that light beams (L1, L2, L3) emitted therefrom may be generally parallel to the longitudinal axis. In some versions, adhesive may be applied between optical fibers (364a, 364b, 365a, 365b, 366a, 366b) and the corresponding optical fiber guide ports (360a, 360b, 361a, 361b, 362a, 362b) and/or between distal lenses (367a, 367b, 368a, 368b, 369a, 369b) and the corresponding optical fiber anchoring chambers (363a, 363b) to assist with securing optical fiber bundles (356a, 356b) to lightboxes (350a, 350b). In any event, optical fiber bundles (356a, 356b) may each direct corresponding light beams (L1, L2, L3) from the proximal light source to the respective lightbox (350a, 350b) and/or from the respective lightbox (350a, 350b) to the proximal light reader, which may be in operative communication with a processor (not shown) for sending data signals thereto based on the light received by the proximal light reader.

While distal lenses (367a, 367b, 368a, 368b, 369a, 369b) of the present version are formed as portions of the respective optical fibers (364a, 364b, 365a, 365b, 366a, 366b), it will be appreciated that each distal lens (367a, 367b, 368a, 368b, 369a, 369b) may be separately formed from the respective optical fiber (364a, 364b, 365a, 365b, 366a, 366b). In some versions, distal lenses (367a, 367b, 368a, 368b, 369a, 369b) may be integrally formed with the respective body (352a, 352b) as a unitary piece. For example, distal lenses (367a, 367b, 368a, 368b, 369a, 369b) may each be molded together with the respective body (352a, 352b). In other versions, distal lenses (367a, 367b, 368a, 368b, 369a, 369b) may be separately formed as individual pieces and secured within the respective optical fiber anchoring chamber (363a, 363b). In such cases, optical fiber guide ports (360a, 360b, 361a, 361b, 362a, 362b) and optical fiber anchoring chambers (363a, 363b) may each be configured to secure optical fiber bundles (356a, 356b) to lightboxes (350a, 350b), respectively, in predetermined positions and/or orientations relative to distal lenses (367a, 367b, 368a, 368b, 369a, 369b).

As shown, each lightbox (350a, 350b) includes a plurality of light reflection elements (also referred to as mirrors) in the form of external angled surfaces (370a, 370b, 371a, 371b, 372a, 372b) of the respective body (352a, 352b), each configured to reflect a corresponding light beam (L1, L2, L3) received thereby. More particularly, each body (352a, 352b) of the present version includes a proximal, transversely outer angled surface (370a, 370b), a longitudinally intermediate, transversely intermediate angled surface (371a, 371b), and a distal, transversely inner angled surface (372a, 372b). As shown, each angled surface (370a, 370b, 371a, 371b, 372a, 372b) is at least partially aligned in the longitudinal direction with a corresponding optical fiber guide port (360a, 360b, 361a, 361b, 362a, 362b) of the respective body (352a, 352b) and thus with a corresponding optical fiber (364a, 364b, 365a, 365b, 366a, 366b) secured therein, and each angled surface (370a, 371a, 372a) of lower body (352a) is also at least partially aligned in the transverse direction with a corresponding, transversely-opposed angled surface (370b, 371b, 372b) of upper body (352b).

In the example shown, each angled surface (370a, 370b, 371a, 371b, 372a, 372b) is obliquely oriented relative to longitudinal axis (A). More particularly, each angled surface (370a, 370b, 371a, 371b, 372a, 372b) of the present version is tapered transversely inwardly in the distal direction. For example, each angled surface (370a, 370b, 371a, 371b, 372a, 372b) may be tapered transversely inwardly in the distal direction at an angle of approximately 45° relative to longitudinal axis (A). In this manner, each angled surface (370a, 370b, 371a, 371b, 372a, 372b) is configured to reflect a corresponding light beam (L1, L2, L3) traveling between angled surface (370a, 370b, 371a, 371b, 372a, 372b) and the optical fiber (364a, 364b, 365a, 365b, 366a, 366b) received within the corresponding optical fiber guide port (360a, 360b, 361a, 361b, 362a, 362b) at an angle of approximately 90° relative to longitudinal axis (A), and is also configured to reflect a corresponding light beam (L1, L2, L3) traveling between angled surface (370a, 370b, 371a, 371b, 372a, 372b) and the corresponding, transversely-opposed angled surface (370a, 370b, 371a, 371b, 372a, 372b) at an angle of approximately 90° relative to longitudinal axis (A).

In the example shown, angled surfaces (370a, 370b, 371a, 371b, 372a, 372b) are each integrally formed with the remainder of the respective body (352a, 352b) as a unitary piece. For example, angled surfaces (370a, 370b, 371a, 371b, 372a, 372b) may each be molded together with the remainder of the respective body (352a, 352b). In this regard, bodies (352a, 352b) may each be constructed of a suitable material to facilitate reflection of light beams (L1, L2, L3) by angled surfaces (370a, 370b, 371a, 371b, 372a, 372b). For example, bodies (352a, 352b) may each be constructed of a plastic material having a density different from that of air, such that the interface between each angled surface (370a, 370b, 371a, 371b, 372a, 372b) and the air external thereof may facilitate the reflection. In some versions, angled surfaces (370a, 370b, 371a, 371b, 372a, 372b) may each be polished to assist with facilitating the reflection. In other versions, a reflective coating, such as a gold coating, may be applied to each angled surface (370a, 370b, 371a, 371b, 372a, 372b) to facilitate the reflection.

As shown, each body (352a, 352b) also includes a light transmission element in the form of an external flat, optically transmissive surface (376a, 376b) that is oriented parallel to longitudinal axis (A) for transmitting light beams (L1, L2, L3) into and/or out of the body (352a, 352b) and configured to face tissue between jaws (320, 322). In this regard, external flat surfaces (376a, 376b) may each be generally orthogonal to light beams (L1, L2, L3) to thereby minimize refraction of light beams (L1, L2, L3) transmitted therethrough. In the example shown, the intersection between each light beam (L1, L2, L3) and each flat surface (376a, 376b) defines an effective sensing location (S1, S2, S3) for the corresponding optical fiber(s) (364a, 364b, 365a, 365b, 366a, 366b) along the respective lightbox (350a, 350b).

In some versions, light beams (L1, L2, L3) may be transmitted from one of the lower or upper lightboxes (350a, 350b) through a medium (e.g., tissue or air) disposed between jaws (320, 322) and received by the other of the lower or upper lightboxes (350a, 350b), so that the processor may determine a type of medium (e.g., tissue or air) disposed between jaws (320, 322) and/or a status of the medium, such as a property of tissue disposed between jaws (320, 322) and/or a position of the tissue relative to end effector (316), based on the light received by the other of the lower or upper lightboxes (350a, 350b). Such a mode of operation may be referred to as transmission sensing.

For example, a first light beam (L1) may be directed through optical fiber (364a) from the proximal light source, emitted from distal lens (367a) of optical fiber (364a) into lower body (352a) generally parallel to longitudinal axis (A), reflected by angled surface (370a) at an angle of approximately 90° to be generally orthogonal to longitudinal axis (A), transmitted out of lower body (352a) via external flat surface (376a) through one or more media (e.g., tissue or air) disposed between external flat surfaces (376a, 376b) and into upper body (352b) via external flat surface (376b), reflected by angled surface (370b) at an angle of approximately 90° to be generally parallel to longitudinal axis (A), emitted from upper body (352b) into distal lens (367b) of optical fiber (364b), and directed through optical fiber (364b) to the proximal light reader. Conversely, first light beam (L1) may be directed through optical fiber (364b) from the proximal light source, emitted from distal lens (367b) of optical fiber (364b) into upper body (352b) generally parallel to longitudinal axis (A), reflected by angled surface (370b) at an angle of approximately 90° to be generally orthogonal to longitudinal axis (A), transmitted out of upper body (352b) via external flat surface (376b) through one or more media (e.g., tissue or air) disposed between external flat surfaces (376a, 376b) and into lower body (352a) via external flat surface (376a), reflected by angled surface (370a) at an angle of approximately 90° to be generally parallel to longitudinal axis (A), emitted from lower body (352a) into distal lens (367a) of optical fiber (364a), and directed through optical fiber (364a) to the proximal light reader.

Likewise, a second light beam (L2) may be directed through optical fiber (365a) from the proximal light source, emitted from distal lens (368a) of optical fiber (365a) into lower body (352a) generally parallel to longitudinal axis (A), reflected by angled surface (371a) at an angle of approximately 90° to be generally orthogonal to longitudinal axis (A), transmitted out of lower body (352a) via external flat surface (376a) through one or more media (e.g., tissue or air) disposed between external flat surfaces (376a, 376b) and into upper body (352b) via external flat surface (376b), reflected by angled surface (371b) at an angle of approximately 90° to be generally parallel to longitudinal axis (A), emitted from upper body (352b) into distal lens (368b) of optical fiber (365b), and directed through optical fiber (365b) to the proximal light reader. Conversely, second light beam (L2) may be directed through optical fiber (365b) from the proximal light source, emitted from distal lens (368b) of optical fiber (365b) into upper body (352b) generally parallel to longitudinal axis (A), reflected by angled surface (371b) at an angle of approximately 90° to be generally orthogonal to longitudinal axis (A), transmitted out of upper body (352b) via external flat surface (376b) through one or more media (e.g., tissue or air) disposed between external flat surfaces (376a, 376b) and into lower body (352a) via external flat surface (376a), reflected by angled surface (371a) at an angle of approximately 90° to be generally parallel to longitudinal axis (A), emitted from lower body (352a) into distal lens (368a) of optical fiber (365a), and directed through optical fiber (365a) to the proximal light reader.

Similarly, a third light beam (L3) may be directed through optical fiber (366a) from the proximal light source, emitted from distal lens (369a) of optical fiber (366a) into lower body (352a) generally parallel to longitudinal axis (A), reflected by angled surface (372a) at an angle of approximately 90° to be generally orthogonal to longitudinal axis (A), transmitted out of lower body (352a) via external flat surface (376a) through one or more media (e.g., tissue or air) disposed between external flat surfaces (376a, 376b) and into upper body (352b) via external flat surface (376b), reflected by angled surface (372b) at an angle of approximately 90° to be generally parallel to longitudinal axis (A), emitted from upper body (352b) into distal lens (369b) of optical fiber (366b), and directed through optical fiber (366b) to the proximal light reader. Conversely, third light beam (L3) may be directed through optical fiber (366b) from the proximal light source, emitted from distal lens (369b) of optical fiber (366b) into upper body (352b) generally parallel to longitudinal axis (A), reflected by angled surface (372b) at an angle of approximately 90° to be generally orthogonal to longitudinal axis (A), transmitted out of upper body (352b) via external flat surface (376b) through one or more media (e.g., tissue or air) disposed between external flat surfaces (376a, 376b) and into lower body (352a) via external flat surface (376a), reflected by angled surface (372a) at an angle of approximately 90° to be generally parallel to longitudinal axis (A), emitted from lower body (352a) into distal lens (369a) of optical fiber (366a), and directed through optical fiber (366a) to the proximal light reader.

In addition, or alternatively, light beams (L1, L2, L3) may be emitted from one of the lower or upper lightboxes (350a, 350b) and reflected by a medium (e.g., tissue) disposed between jaws (320, 322) back into the same lightbox (350a, 350b), so that the processor may determine a type of medium (e.g., tissue or air) disposed between jaws (320, 322) and/or a status of the medium, such as a property of tissue disposed between jaws (320, 322) and/or a position of the tissue relative to end effector (316), based on the light received by the same lightbox (350a, 350b). Such a mode of operation may be referred to as reflectance sensing.

For example, first light beam (L1) may be directed through optical fiber (364a) from the proximal light source, emitted from distal lens (367a) of optical fiber (364a) into lower body (352a) generally parallel to longitudinal axis (A), reflected by angled surface (370a) at an angle of approximately 90° to be generally orthogonal to longitudinal axis (A), transmitted out of lower body (352a) via external flat surface (376a), reflected by one or more media (e.g., tissue) disposed between external flat surfaces (376a, 376b) back into lower body (352a) via external flat surface (376a), reflected by angled surface (370a) at an angle of approximately 90° to be generally parallel to longitudinal axis (A), emitted from lower body (352a) into distal lens (367a) of optical fiber (364a), and directed through optical fiber (364a) to the proximal light reader. In addition, or alternatively, first light beam (L1) may be directed through optical fiber (364b) from the proximal light source, emitted from distal lens (367b) of optical fiber (364b) into upper body (352b) generally parallel to longitudinal axis (A), reflected by angled surface (370b) at an angle of approximately 90° to be generally orthogonal to longitudinal axis (A), transmitted out of upper body (352b) via external flat surface (376b), reflected by one or more media (e.g., tissue) disposed between external flat surfaces (376a, 376b) back into upper body (352b) via external flat surface (376b), reflected by angled surface (370b) at an angle of approximately 90° to be generally parallel to longitudinal axis (A), emitted from upper body (352b) into distal lens (367b) of optical fiber (364b), and directed through optical fiber (364b) to the proximal light reader.

Likewise, second light beam (L2) may be directed through optical fiber (365a) from the proximal light source, emitted from distal lens (368a) of optical fiber (365a) into lower body (352a) generally parallel to longitudinal axis (A), reflected by angled surface (371a) at an angle of approximately 90° to be generally orthogonal to longitudinal axis (A), transmitted out of lower body (352a) via external flat surface (376a), reflected by one or more media (e.g., tissue) disposed between external flat surfaces (376a, 376b) back into lower body (352a) via external flat surface (376a), reflected by angled surface (371a) at an angle of approximately 90° to be generally parallel to longitudinal axis (A), emitted from lower body (352a) into distal lens (368a) of optical fiber (365a), and directed through optical fiber (365a) to the proximal light reader. In addition, or alternatively, second light beam (L2) may be directed through optical fiber (365b) from the proximal light source, emitted from distal lens (368b) of optical fiber (365b) into upper body (352b) generally parallel to longitudinal axis (A), reflected by angled surface (371b) at an angle of approximately 90° to be generally orthogonal to longitudinal axis (A), transmitted out of upper body (352b) via external flat surface (376b), reflected by one or more media (e.g., tissue) disposed between external flat surfaces (376a, 376b) back into upper body (352b) via external flat surface (376b), reflected by angled surface (371b) at an angle of approximately 90° to be generally parallel to longitudinal axis (A), emitted from upper body (352b) into distal lens (368b) of optical fiber (365b), and directed through optical fiber (365b) to the proximal light reader.

Similarly, third light beam (L3) may be directed through optical fiber (366a) from the proximal light source, emitted from distal lens (369a) of optical fiber (366a) into lower body (352a) generally parallel to longitudinal axis (A), reflected by angled surface (372a) at an angle of approximately 90° to be generally orthogonal to longitudinal axis (A), transmitted out of lower body (352a) via external flat surface (376a), reflected by one or more media (e.g., tissue) disposed between external flat surfaces (376a, 376b) back into lower body (352a) via external flat surface (376a), reflected by angled surface (372a) at an angle of approximately 90° to be generally parallel to longitudinal axis (A), emitted from lower body (352a) into distal lens (369a) of optical fiber (366a), and directed through optical fiber (366a) to the proximal light reader. In addition, or alternatively, third light beam (L3) may be directed through optical fiber (366b) from the proximal light source, emitted from distal lens (369b) of optical fiber (366b) into upper body (352b) generally parallel to longitudinal axis (A), reflected by angled surface (372b) at an angle of approximately 90° to be generally orthogonal to longitudinal axis (A), transmitted out of upper body (352b) via external flat surface (376b), reflected by one or more media (e.g., tissue or air) disposed between external flat surfaces (376a, 376b) back into upper body (352b) via external flat surface (376b), reflected by angled surface (372b) at an angle of approximately 90° to be generally parallel to longitudinal axis (A), emitted from upper body (352b) into distal lens (369b) of optical fiber (366b), and directed through optical fiber (366b) to the proximal light reader.

It will be appreciated that upper and lower lightboxes (350a, 350b) may be alternatively utilized to perform transmission sensing and reflectance sensing. For example, the processor may be in operative communication with the proximal light source and the proximal light reader to send control signals thereto for alternating between each mode of operation. In some versions, one of the upper or lower lightboxes (350a, 350b) may be omitted and the other of the upper or lower lightboxes (350a, 350b) may be utilized for reflectance sensing.

B. Exemplary Optical Sensing Lightbox with Multi-Mode Optical Fiber

Figure 9:
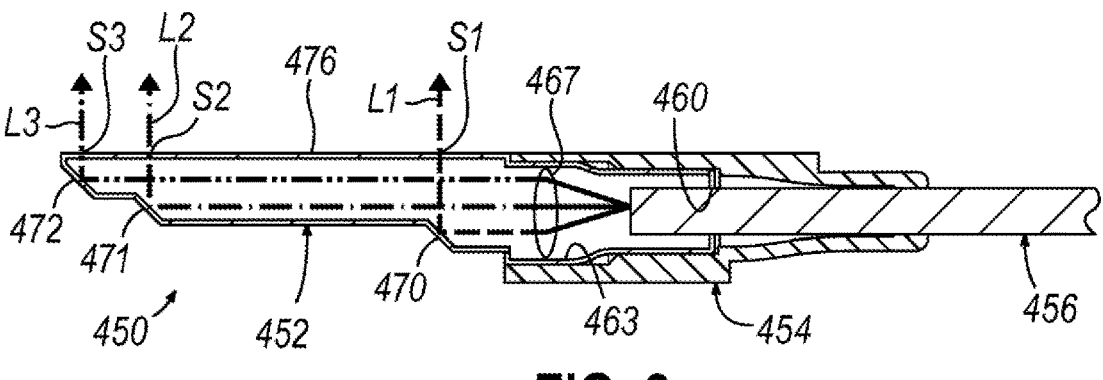
FIG. 9 depicts a cross-sectional side view of another exemplary lightbox, taken along a centerline thereof, coupled to an optical fiber bundle, showing light beams emitted from the optical fiber bundle collimated by a lens and reflected by corresponding light reflection elements of the lightbox.

FIG. 9 shows another exemplary optical sensing lightbox (450) for use with electrosurgical instrument (302). Lightbox (450) is similar to lightboxes (350a, 350b) described above except as otherwise described below. In this regard, lightbox (450) of this example may be received within recess (346, 348) of either jaw (320, 322) of end effector (316) in place of one or both lightboxes (350a, 350b).

As shown, lightbox (450) includes a housing in the form of a distal hollow body (452) fixedly coupled to a proximal cover (454) and is configured to transmit light to and/or receive light from an illuminating and/or light receiving element in the form of a multi-mode optical fiber (456), which is operatively coupled to a proximal light source and/or proximal light reader (not shown). In this regard, hollow body (452) includes an optical fiber guide port (460) extending through a proximal end thereof for receiving a distal portion of optical fiber (456) to thereby anchor or otherwise secure optical fiber (456) to lightbox (450) in a predetermined position and/or orientation relative to lightbox (450). For example, at least a distal portion of optical fiber (456) may be generally parallel to a longitudinal axis of body (452). Optical fiber guide port (460) of the present version communicates with an internal chamber (463) of hollow body (452). Internal chamber (463) is configured to receive a collimating lens (467) disposed distal of optical fiber (456), such that optical fiber (456) may direct a plurality of light beams (L1, L2, L3) from the proximal light source to collimating lens (467) and/or from collimating lens (467) to the proximal light reader, which may be in operative communication with a processor (not shown) for sending data signals thereto based on the light received by the proximal light reader. As shown, collimating lens (467) may be spaced apart from a distal end of optical fiber (456).

While collimating lens (467) of the present version is separately formed as an individual piece and secured within chamber (463), it will be appreciated that collimating lens (467) may be integrally formed with body (452) as a unitary piece. For example, collimating lens (467) may be molded together with body (452). In any event, optical fiber guide port (460) and chamber (463) may each be configured to secure optical fiber (456) to lightbox (450) in a predetermined position and/or orientation relative to collimating lens (467).

As shown, lightbox (450) includes a plurality of light reflection elements (also referred to as mirrors) in the form of internal angled surfaces (470, 471, 472) of hollow body (352a, 352b), each configured to reflect a corresponding light beam (L1, L2, L3) received thereby. More particularly, hollow body (452) of the present version includes a proximal, transversely outer angled surface (470), a longitudinally intermediate, transversely intermediate angled surface (471), and a distal, transversely inner angled surface (472). As shown, each angled surface (470, 471, 472) is at least partially aligned in the longitudinal direction with collimating lens (467). While not shown, each angled surface (470, 471, 472) of hollow body (452) may also be at least partially aligned in the transverse direction with a corresponding, transversely-opposed angled surface of a hollow body of a similarly configured lightbox in a manner similar to that described above in connection with FIGS. 6-8.

In the example shown, each angled surface (470, 471, 472) is obliquely oriented relative to a longitudinal axis of hollow body (452). More particularly, each angled surface (470, 471, 472) of the present version is tapered transversely inwardly in the distal direction. For example, each angled surface (470, 471, 472) may be tapered transversely inwardly in the distal direction at an angle of approximately 45° relative to the longitudinal axis. In this manner, each angled surface (470, 471, 472) is configured to reflect a corresponding light beam (L1, L2, L3) traveling between angled surface (470, 471, 472) and the optical fiber (456) received within optical fiber guide port (460) at an angle of approximately 90° relative to the longitudinal axis, and is also configured to reflect a corresponding light beam (L1, L2, L3) traveling between angled surface (470, 471, 472) and the corresponding, transversely-opposed angled surface of a similarly configured lightbox (not shown) at an angle of approximately 90° relative to the longitudinal axis.

In the example shown, angled surfaces (470, 471, 472) are each integrally formed with the remainder of hollow body (452) as a unitary piece. For example, angled surfaces (470, 471, 472) may each be molded together with the remainder of hollow body (452). In this regard, hollow body (452) may be constructed of a suitable material to facilitate reflection of light beams (L1, L2, L3) by angled surfaces (470, 471, 472). For example, hollow body (452) may be constructed of a plastic material having a density different from that of air, such that the interface between each angled surface (470, 471, 472) and the air within chamber (463) may facilitate the reflection. In some versions, hollow body (452) may comprise a material having an opacity configured to allow the passage of light therethrough, such as a translucent and/or transparent material. In addition, or alternatively, angled surfaces (470, 471, 472) may each be polished to assist with facilitating the reflection. In other versions, a reflective coating, such as a gold coating, may be applied to each angled surface (470, 471, 472) to facilitate the reflection.

As shown, hollow body (452) also includes a light transmission element in the form of a flat wall (476) defining an optically transmissive surface that is oriented parallel to the longitudinal axis for transmitting light beams (L1, L2, L3) into and/or out of the hollow body (452) and configured to face tissue between jaws (320, 322). In this regard, flat wall (476) may be generally orthogonal to light beams (L1, L2, L3) to thereby minimize refraction of light beams (L1, L2, L3) transmitted therethrough. In the example shown, the intersection between each light beam (L1, L2, L3) and flat wall (476) defines an effective sensing location (S1, S2, S3) for optical fiber (456) along lightbox (450).

In a transmission mode of operation, light beams (L1, L2, L3) may be transmitted from lightbox (450) through a medium (e.g., tissue or air) disposed between jaws (320, 322) and received by another similarly configured lightbox (not shown), in a manner similar to that described above in connection with FIGS. 6-7. In a reflectance mode of operation, light beams (L1, L2, L3) may be emitted from lightbox (450) and reflected by a medium (e.g., tissue) disposed between jaws (320, 322) back into lightbox (450), in a manner similar to that described above in connection with FIGS. 6-7. For example, light may be directed through optical fiber (456) from the proximal light source, emitted from a distal end of optical fiber (456) toward collimating lens (467), and collimated or otherwise conditioned by collimating lens (467) into a plurality of light beams (L1, L2, L3) generally parallel to the longitudinal axis, which may each be reflected by a corresponding angled surface (470, 471, 472) at an angle of approximately 90° to be generally orthogonal to the longitudinal axis, transmitted out of hollow body (452) via flat wall (476), and either transmitted through one or more media (e.g., tissue or air) disposed external to flat wall (476) and received by a similarly configured, transversely-opposed lightbox (not shown) or reflected by the one or more media back into lightbox (450) in a manner(s) similar to that described above in connection with FIGS. 6-7.

C. Exemplary Optical Sensing Lightbox with Parabolic Reflectors

Figure 10:
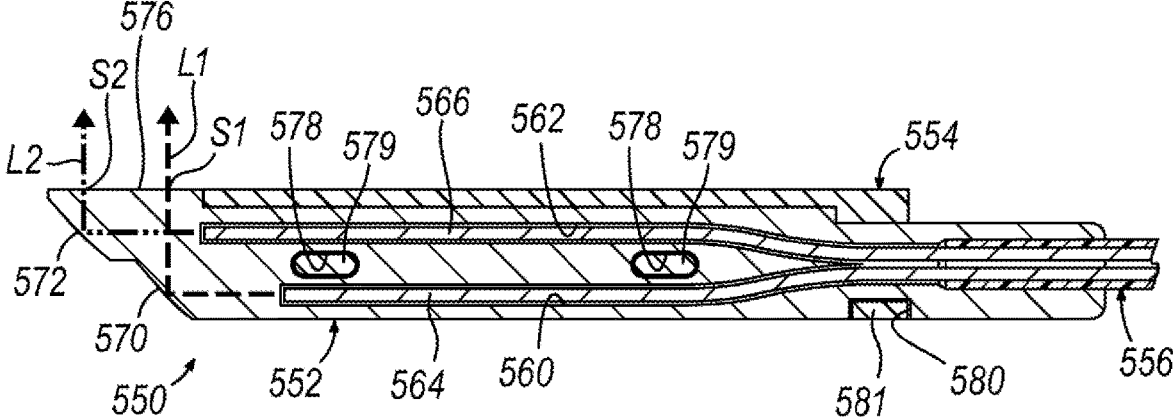
FIG. 10 depicts a cross-sectional side view of another exemplary lightbox, taken along a centerline thereof, coupled to an optical fiber bundle, showing light beams emitted from the optical fiber bundle reflected by corresponding light reflection elements of the lightbox.

FIG. 10 shows another exemplary optical sensing lightbox (550) for use with electrosurgical instrument (302). Lightbox (550) is similar to lightboxes (350a, 350b) described above except as otherwise described below. In this regard, lightbox (550) of this example may be received within recess (346, 348) of either jaw (320, 322) of end effector (316) in place of one or both lightboxes (350a, 350b).

As shown, lightbox (550) includes a housing in the form of a distal body (552) removably coupled to a proximal cover (554) and is configured to transmit light to and/or receive light from an illuminating and/or light receiving element in the form of an optical fiber bundle (556), which is operatively coupled to a proximal light source and/or proximal light reader (not shown). In this regard, body (552) may comprise a material having an opacity configured to allow the passage of light therethrough, such as a translucent and/or transparent material, and includes a plurality of optical fiber guide ports (560, 562) extending distally from a proximal end thereof for receiving respective portions of optical fiber bundle (556). More particularly, body (552) of the present version includes a proximal, transversely outer optical fiber guide port (560) and a distal, transversely inner optical fiber guide port (562).

Each optical fiber guide port (560, 562) is configured to receive a respective optical fiber (564, 566) of optical fiber bundle (556) to thereby anchor or otherwise secure optical fiber bundle (556) to lightbox (550) in a predetermined position and/or orientation relative to lightbox (550). For example, at least a distal portion of each optical fiber (564, 566) may be generally parallel to a longitudinal axis of body (552) such that light beams (L1, L2) emitted therefrom may be generally parallel to the longitudinal axis. In some versions, adhesive may be applied between optical fibers (564, 566) and the corresponding optical fiber guide ports (560, 562) to assist with securing optical fiber bundle (556)

to lightbox (550). In any event, optical fiber bundle (556) may direct light beams (L1, L2) from the proximal light source to lightbox (550) and/or from lightbox (550) to the proximal light reader, which may be in operative communication with a processor (not shown) for sending data signals thereto based on the light received by the proximal light reader.

As shown, lightbox (550) includes a plurality of light reflection elements (also referred to as mirrors) in the form of external parabolic surfaces (570, 572) of body (552), each configured to reflect a corresponding light beam (L1, L2) received thereby. More particularly, body (552) of the present version includes a proximal, transversely outer parabolic surface (570) and a distal, transversely inner parabolic surface (572). As shown, each parabolic surface (570, 572) is at least partially aligned in the longitudinal direction with a corresponding optical fiber guide port (560, 562) of body (552) and thus with a corresponding optical fiber (564, 566) secured therein. While not shown, each parabolic surface (570, 572) of body (552) may also be at least partially aligned in the transverse direction with a corresponding, transversely-opposed parabolic surface of a body of a similarly configured lightbox in a manner similar to that described above in connection with FIGS. 6-8.

In the example shown, each parabolic surface (570, 572) is curved transversely inwardly in the distal direction and has a generally convex configuration. In this manner, each parabolic surface (570, 572) is configured to reflect a corresponding light beam (L1, L2) traveling between parabolic surface (570, 572) and the optical fiber (564, 566) received within the corresponding optical fiber guide port (560, 562) at an angle of approximately 90° relative to the longitudinal axis, and is also configured to reflect a corresponding light beam (L1, L2) traveling between parabolic surface (570, 572) and the corresponding, transversely-opposed parabolic surface of a similarly configured lightbox (not shown) at an angle of approximately 90° relative to the longitudinal axis.

In the example shown, parabolic surfaces (570, 572) are each integrally formed with the remainder of body (552) as a unitary piece. For example, parabolic surfaces (570, 572) may each be molded together with the remainder of body (552). In this regard, body (552) may be constructed of a suitable material to facilitate reflection of light beams (L1, L2) by parabolic surfaces (570, 572). For example, body (552) may be constructed of a plastic material having a density different from that of air, such that the interface between each parabolic surface (570, 572) and the air external thereto may facilitate the reflection. In some versions, parabolic surfaces (570, 572) may each be polished to assist with facilitating the reflection. In other versions, a reflective coating, such as a gold coating, may be applied to each parabolic surface (570, 572) to facilitate the reflection. In any event, it will be appreciated that the curvature of each parabolic surface (570, 572) may facilitate conditioning/altering (e.g., focusing) of light beams (L1, L2) in addition to reflection thereof.

As shown, body (552) also includes a light transmission element in the form of an external flat, optically transmissive surface (576) that is oriented parallel to the longitudinal axis for transmitting light beams (L1, L2) into and/or out of body (552) and configured to face tissue between jaws (320, 322). In this regard, external flat surface (576) may be generally orthogonal to light beams (L1, L2) to thereby minimize refraction of light beams (L1, L2) transmitted therethrough. In the example shown, the intersection between each light beam (L1, L2) and flat surface (576) defines an effective sensing location (S1, S2) for the corresponding optical fiber (564, 566) along lightbox (550). Body (552) of the present version further includes a pair of laterally-extending apertures (578) configured to receive a corresponding pair of laterally-extending detents (579) of cover (554) and a proximal recess (580) configured to receive a corresponding proximal tab (581) of cover (554) for removably coupling cover (554) to body (552).

In a transmission mode of operation, light beams (L1, L2) may be transmitted from lightbox (550) through a medium (e.g., tissue or air) disposed between jaws (320, 322) and received by another similarly configured lightbox (not shown), in a manner similar to that described above in connection with FIGS. 6-7. In a reflectance mode of operation, light beams (L1, L2) may be emitted from lightbox (550) and reflected by a medium (e.g., tissue) disposed between jaws (320, 322) back into lightbox (550), in a manner similar to that described above in connection with FIGS. 6-7. For example, light beams (L1, L2) may be directed through corresponding optical fibers (564, 566) from the proximal light source, emitted from distal ends of optical fibers (564, 566) into body (552) generally parallel to the longitudinal axis, reflected by a corresponding angled surface (570, 572) at an angle of approximately 90° to be generally orthogonal to the longitudinal axis, transmitted out of body (552) via flat surface (576), and either transmitted through one or more media (e.g., tissue or air) disposed external to flat surface (576) and received by a similarly configured, transversely-opposed lightbox (not shown) or reflected by the one or more media back into lightbox (550) in a manner(s) similar to that described above in connection with FIGS. 6-7.

D. Exemplary Optical Sensing Lightbox with Parabolic Reflectors and Raw Fiber

Figure 11:
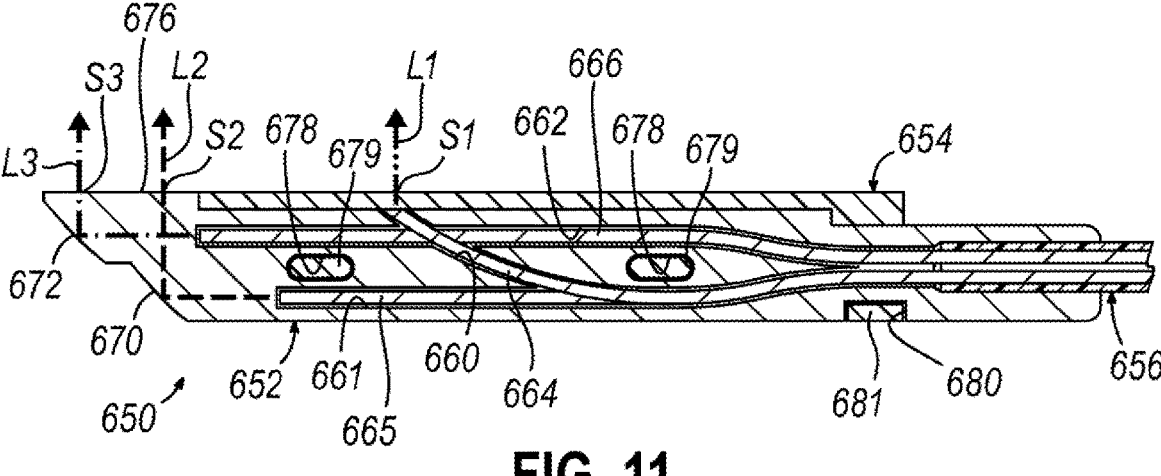
FIG. 11 depicts a cross-sectional side view of another exemplary lightbox, taken along a centerline thereof, coupled to an optical fiber bundle, showing light beams emitted from straight optical fibers of the optical fiber bundle reflected by corresponding light reflection elements of the lightbox, and showing a light beam emitted from a curved optical fiber of the optical fiber bundle without being reflected by any light reflection element of the lightbox.

FIG. 11 shows another exemplary optical sensing lightbox (650) for use with electrosurgical instrument (302). Lightbox (650) is similar to lightboxes (350a, 350b) described above except as otherwise described below. In this regard, lightbox (650) of this example may be received within recess (346, 348) of either jaw (320, 322) of end effector (316) in place of one or both lightboxes (350a, 350b).

As shown, lightbox (650) includes a housing in the form of a distal body (652) removably coupled to a proximal cover (654) and is configured to transmit light to and/or receive light from an illuminating and/or light receiving element in the form of an optical fiber bundle (656), which is operatively coupled to a proximal light source and/or proximal light reader (not shown). In this regard, body (652) may comprise a material having an opacity configured to allow the passage of light therethrough, such as a translucent and/or transparent material, and includes a plurality of optical fiber guide ports (660, 661, 662) extending distally from a proximal end thereof for receiving respective portions of optical fiber bundle (656). More particularly, body (652) of the present version includes a proximal optical fiber guide port (660), a longitudinally intermediate optical fiber guide port (661), and a distal optical fiber guide port (662). Cover (654) may also comprise a material having an opacity configured to allow the passage of light therethrough.

Each optical fiber guide port (660, 661, 662) is configured to receive a respective optical fiber (664, 665, 666) of optical fiber bundle (656) to thereby anchor or otherwise secure optical fiber bundle (656) to lightbox (650) in a predetermined position and/or orientation relative to lightbox (650). For example, a distal portion of optical fiber (664) may be curved transversely inwardly in the distal direction such that a light beam (L1) emitted therefrom may be oriented at an angle of approximately 90° relative to a longitudinal axis of body (652), while at least a distal portion of each optical fiber (665, 666) may be generally parallel to the longitudinal axis such that light beams (L2, L3) emitted therefrom may be generally parallel to the longitudinal axis. In some versions, adhesive may be applied between optical fibers (664, 665, 666) and the corresponding optical fiber guide ports (660, 661, 662) to assist with securing optical fiber bundle (656) to lightbox (650). In any event, optical fiber bundle (656) may direct light beams (L1, L2, L3) from the proximal light source to lightbox (650) and/or from lightbox (650) to the proximal light reader, which may be in operative communication with a processor (not shown) for sending data signals thereto based on the light received by the proximal light reader.

It will be appreciated that optical fiber (664) may have a bend radius configured to facilitate emission of light beam (L1) therefrom at an angle of approximately 90° relative to the longitudinal axis, such that optical fiber (664) may be considered a "raw" fiber without any additional light reflection element of lightbox (650) included for reflecting light beam (L1). It will also be appreciated that cover (654) may serve as a light transmission element defining an optically transmissive surface oriented parallel to the longitudinal axis for transmitting light beam (L1) into and/or out of lightbox (650) and configured to face tissue between jaws (320, 322). In this regard, cover (654) may be generally orthogonal to light beam (L1) to thereby minimize refraction of light beam (L1) transmitted therethrough. In some versions, cover (654) may have any suitable optical properties to facilitate conditioning/altering (e.g., focusing) of light beam (L1) in a desired manner. In the example shown, the intersection between light beam (L1) and cover (654) defines an effective sensing location (S1) for optical fiber (664) along lightbox (650).

As shown, lightbox (650) includes a plurality of light reflection elements (also referred to as mirrors) in the form of external parabolic surfaces (670, 672) of body (652), each configured to reflect a corresponding light beam (L2, L3) received thereby. More particularly, body (652) of the present version includes a proximal, transversely outer parabolic surface (670) and a distal, transversely inner parabolic surface (672). As shown, each parabolic surface (670, 672) is at least partially aligned in the longitudinal direction with a corresponding optical fiber guide port (661, 662) of body (652) and thus with a corresponding optical fiber (665, 666) secured therein. While not shown, each parabolic surface (670, 672) of body (652) may also be at least partially aligned in the transverse direction with a corresponding, transversely-opposed parabolic surface of a body of a similarly configured lightbox in a manner similar to that described above in connection with FIGS. 6-8.

In the example shown, each parabolic surface (670, 672) is curved transversely inwardly in the distal direction and has a generally convex configuration. In this manner, each parabolic surface (670, 672) is configured to reflect a corresponding light beam (L2, L3) traveling between parabolic surface (670, 672) and the optical fiber (665, 666) received within the corresponding optical fiber guide port (661, 662) at an angle of approximately 90° relative to the longitudinal axis, and is also configured to reflect a corresponding light beam (L2, L3) traveling between parabolic surface (670, 672) and the corresponding, transversely-opposed parabolic surface of a similarly configured lightbox (not shown) at an angle of approximately 90° relative to the longitudinal axis.

In the example shown, parabolic surfaces (670, 672) are each integrally formed with the remainder of body (652) as a unitary piece. For example, parabolic surfaces (670, 672)

may each be molded together with the remainder of body (652). In this regard, body (652) may be constructed of a suitable material to facilitate reflection of light beams (L2, L3) by parabolic surfaces (670, 672). For example, body (652) may be constructed of a plastic material having a density different from that of air, such that the interface between each parabolic surface (670, 672) and the air external thereto may facilitate the reflection. In some versions, parabolic surfaces (670, 672) may each be polished to assist with facilitating the reflection. In other versions, a reflective coating, such as a gold coating, may be applied to each parabolic surface (670, 672) to facilitate the reflection. In any event, it will be appreciated that the curvature of each parabolic surface (670, 672) may facilitate conditioning/altering (e.g., focusing) of light beams (L2, L3) in addition to reflection thereof.

As shown, body (652) also includes a light transmission element in the form of an external flat, optically transmissive surface (676) that is oriented parallel to the longitudinal axis for transmitting light beams (L2, L3) into and/or out of body (652) and configured to face tissue between jaws (320, 322). In this regard, external flat surface (676) may be generally orthogonal to light beams (L2, L3) to thereby minimize refraction of light beams (L2, L3) transmitted therethrough. In the example shown, the intersection between each light beam (L2, L3) and flat surface (676) defines an effective sensing location (S2, S3) for the corresponding optical fiber (665, 666) along lightbox (650). Body (652) of the present version further includes a pair of laterally-extending apertures (678) configured to receive a corresponding pair of laterally-extending detents (679) of cover (654) and a proximal recess (680) configured to receive a corresponding proximal tab (681) of cover (654) for removably coupling cover (654) to body (652).

In a transmission mode of operation, light beams (L1, L2, L3) may be transmitted from lightbox (650) through a medium (e.g., tissue or air) disposed between jaws (320, 322) and received by another similarly configured lightbox (not shown), in a manner similar to that described above in connection with FIGS. 6-7. In a reflectance mode of operation, light beams (L1, L2, L3) may be emitted from lightbox (650) and reflected by a medium (e.g., tissue) disposed between jaws (320, 322) back into lightbox (650), in a manner similar to that described above in connection with FIGS. 6-7. In a hybrid mode of operation, light beam (L1) may be emitted from lightbox (650) and reflected by a medium (e.g., tissue) disposed between jaws (320, 322) back into lightbox (650), and light beams (L2, L3) may be transmitted from lightbox (650) through a medium (e.g., tissue or air) disposed between jaws (320, 322) and received by another similarly configured lightbox (not shown). For example, light beam (L1) may be directed through optical fiber (664) from the proximal light source, emitted from a distal end of optical fiber (664) through cover (654) generally orthogonal to the longitudinal axis, and reflected by one or more media (e.g., tissue or air) disposed external to cover (654) back into lightbox (650) in a manner similar to that described above in connection with FIGS. 6-7. Concurrently, light beams (L2, L3) may be directed through corresponding optical fibers (665, 666) from the proximal light source, emitted from distal ends of optical fibers (665, 666) into body (652) generally parallel to the longitudinal axis, reflected by a corresponding angled surface (670, 672) at an angle of approximately 90° to be generally orthogonal to the longitudinal axis, transmitted out of body (652) via flat surface (676), and transmitted through one or more media (e.g., tissue or air) disposed external to flat surface (676) and received by a similarly configured, transversely-opposed lightbox (not shown) in a manner similar to that described above in connection with FIGS. 6-7.

E. Exemplary Optical Sensing Lightbox with Raw Fiber

Figure 12:
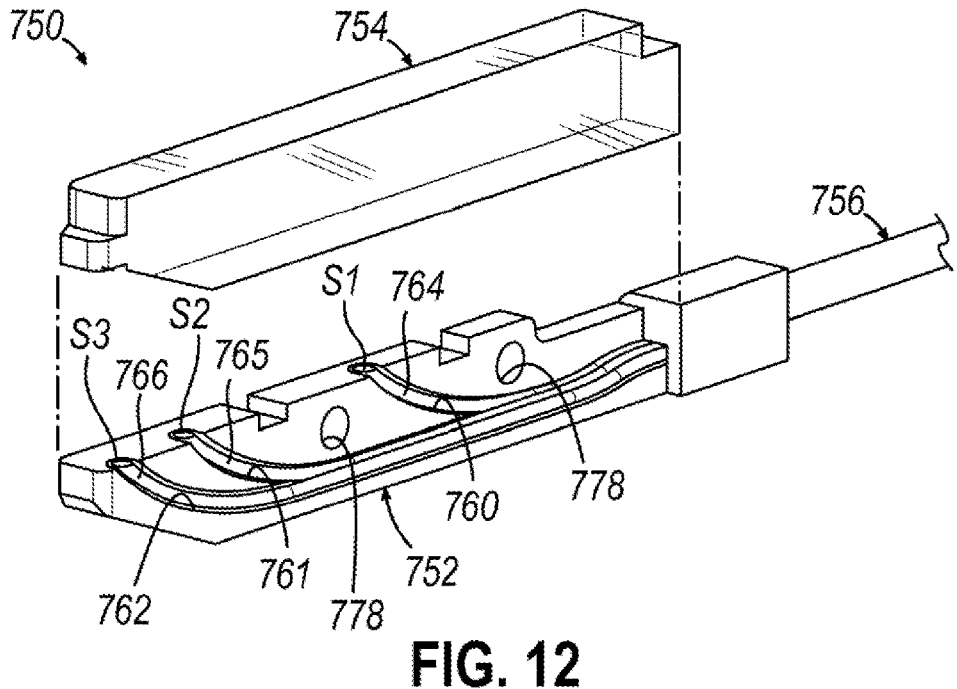
FIG. 12 depicts an exploded view of another exemplary lightbox coupled to an optical fiber bundle, showing optical fibers of the optical fiber bundled curved within the lightbox.

FIG. 12 shows another exemplary optical sensing lightbox (750) for use with electrosurgical instrument (302). Lightbox (750) is similar to lightboxes (350a, 350b) described above except as otherwise described below. In this regard, lightbox (750) of this example may be received within recess (346, 348) of either jaw (320, 322) of end effector (316) in place of one or both lightboxes (350a, 350b).

As shown, lightbox (750) includes a housing in the form of a distal body (752) removably coupled to a proximal cover (754) and is configured to transmit light to and/or receive light from an illuminating and/or light receiving element in the form of an optical fiber bundle (756), which is operatively coupled to a proximal light source and/or proximal light reader (not shown). In this regard, body (752) includes a plurality of optical fiber guide ports (760, 761, 762) extending distally from a proximal end thereof for receiving respective portions of optical fiber bundle (756). More particularly, body (752) of the present version includes a proximal optical fiber guide port (760), a longitudinally intermediate optical fiber guide port (761), and a distal optical fiber guide port (762). Cover (754) may comprise a material having an opacity configured to allow the passage of light therethrough, such as a translucent and/or transparent material.

Each optical fiber guide port (760, 761, 762) is configured to receive a respective optical fiber (764, 765, 766) of optical fiber bundle (756) to thereby anchor or otherwise secure optical fiber bundle (756) to lightbox (750) in a predetermined position and/or orientation relative to lightbox (750). For example, a distal portion of each optical fiber (764, 765, 766) may be curved transversely inwardly in the distal direction such that respective light beams (not shown) emitted therefrom may be oriented at an angle of approximately 90° relative to a longitudinal axis of body (752). In some versions, adhesive may be applied between optical fibers (764, 765, 766) and the corresponding optical fiber guide ports (760, 761, 762) to assist with securing optical fiber bundle (756) to lightbox (750). In any event, optical fiber bundle (756) may direct light beams from the proximal light source to lightbox (750) and/or from lightbox (750) to the proximal light reader, which may be in operative communication with a processor (not shown) for sending data signals thereto based on the light received by the proximal light reader.

It will be appreciated that optical fibers (764, 765, 766) may each have a bend radius configured to facilitate emission of respective light beams therefrom at an angle of approximately 90° relative to the longitudinal axis, such that optical fibers (764, 765, 766) may each be considered a "raw" fiber without any additional light reflection element of lightbox (750) included for reflecting the light beams. It will also be appreciated that cover (754) may serve as a light transmission element defining an optically transmissive surface oriented parallel to the longitudinal axis for transmitting such light beams into and/or out of lightbox (750) and configured to face tissue between jaws (320, 322). In this regard, cover (754) may be generally orthogonal to such light beams to thereby minimize refraction of the light beams transmitted therethrough. In some versions, cover (754) may have any suitable optical properties to facilitate conditioning/altering (e.g., focusing) of the light beams in a desired manner. In the example shown, the intersection between each light beam and cover (754) defines an effective sensing location (S1, S2, S3) for the corresponding optical fiber (764, 765, 766) along lightbox (750). Body (752) of the present version further includes a pair of laterally-extending apertures (778) configured to receive a corresponding pair of laterally-extending detents (not shown) of cover (754) for removably coupling cover (754) to body (752).

In a transmission mode of operation, light beams may be transmitted from lightbox (750) through a medium (e.g., tissue or air) disposed between jaws (320, 322) and received by another similarly configured lightbox (not shown), in a manner similar to that described above in connection with FIGS. 6-7. In a reflectance mode of operation, light beams may be emitted from lightbox (750) and reflected by a medium (e.g., tissue) disposed between jaws (320, 322) back into lightbox (750), in a manner similar to that described above in connection with FIGS. 6-7. For example, light beams may be directed through corresponding optical fibers (764, 765, 766) from the proximal light source, emitted from distal ends of optical fibers (764, 765, 766) into cover (754) generally orthogonal to the longitudinal axis, and either transmitted through one or more media (e.g., tissue or air) disposed external to cover (754) and received by a similarly configured, transversely-opposed lightbox (not shown) or reflected by the one or more media back into lightbox (750) in a manner(s) similar to that described above in connection with FIGS. 6-7.

F. Exemplary Optical Sensing Lightbox with VSCEL Array

Figure 13:
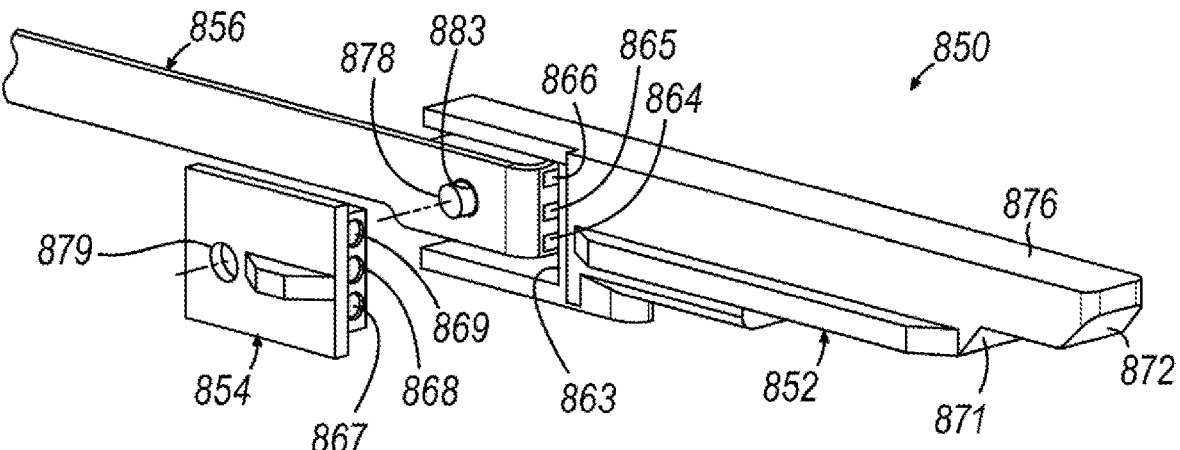
FIG. 13 depicts an exploded view of another exemplary lightbox coupled to a substrate carrying an array of vertical-cavity surface-emitting lasers (VCSELs)

FIG. 13 shows another exemplary optical sensing lightbox (850) for use with electrosurgical instrument (302). Lightbox (850) is similar to lightboxes (350a, 350b) described above except as otherwise described below. In this regard, lightbox (850) of this example may be received within recess (346, 348) of either jaw (320, 322) of end effector (316) in place of one or both lightboxes (350a, 350b).

As shown, lightbox (850) includes a housing in the form of a distal body (852) removably coupled to a proximal cover (854) and configured to receive light from a laser diode-carrying substrate (856). In this regard, body (852) may comprise a material having an opacity configured to allow the passage of light therethrough, such as a translucent and/or transparent material, and includes a chamber (863) configured to receive a distal portion of substrate (856) carrying an array of illuminating elements in the form of laser diodes and, more particularly, vertical-cavity surface-emitting lasers (VCSELs) (864, 865, 866) to thereby anchor or otherwise secure substrate (856) to lightbox (850) in a predetermined position and/or orientation relative to lightbox (850). For example, each VCSEL (864, 865, 866) may define a central axis generally parallel to a longitudinal axis of body (852) such that light beams (not shown) emitted therefrom may be generally parallel to the longitudinal axis. Chamber (863) of the present version is also configured to receive an array of lenses (867, 868, 869) carried by cover (854), such that each VCSEL (864, 865, 866) may emit a respective light beam toward a corresponding lens (867, 868, 869). In this regard, chamber (863) may be configured to secure substrate (856) to lightbox (850) in a predetermined position and/or orientation relative to lenses (867, 868, 869).

As shown, lightbox (850) includes a plurality of light reflection elements (also referred to as mirrors) in the form of external angled surfaces (871, 872) of body (852), each configured to reflect a corresponding light beam received thereby. More particularly, body (852) of the present version includes a proximal, transversely outer angled surface (not shown), a longitudinally intermediate, transversely intermediate angled surface (871) and a distal, transversely inner angled surface (872). As shown, each angled surface (871, 872) is at least partially aligned in the longitudinal direction with a corresponding VCSEL (864, 865, 866) as well as the respective lens (867, 868, 869). While not shown, each angled surface (871, 872) of body (852) may also be at least partially aligned in the transverse direction with a corresponding, transversely-opposed angled surface of a body of another lightbox in a manner similar to that described above in connection with FIGS. 6-8.

In the example shown, each angled surface (871, 872) is obliquely oriented relative to the longitudinal axis. More particularly, each angled surface (871, 872) of the present version is tapered transversely inwardly in the distal direction. For example, each angled surface (871, 872) may be tapered transversely inwardly in the distal direction at an angle of approximately 45° relative to the longitudinal axis. In this manner, each angled surface (871, 872) is configured to reflect a corresponding light beam traveling between angled surface (871, 872) and the corresponding VCSEL (864, 865, 866) at an angle of approximately 90° relative to the longitudinal axis, and is also configured to reflect a corresponding light beam traveling between angled surface (871, 872) and the corresponding, transversely-opposed angled surface of another lightbox (not shown) at an angle of approximately 90° relative to the longitudinal axis.

In the example shown, angled surfaces (871, 872) are each integrally formed with the remainder of body (852) as a unitary piece. For example, angled surfaces (871, 872) may each be molded together with the remainder of body (852). In this regard, body (852) may be constructed of a suitable material to facilitate reflection of light beams by angled surfaces (871, 872). For example, body (852) may be constructed of a plastic material having a density different from that of air, such that the interface between each angled surface (871, 872) and the air external thereof may facilitate the reflection. In some versions, angled surfaces (871, 872) may each be polished to assist with facilitating the reflection. In other versions, a reflective coating, such as a gold coating, may be applied to each angled surface (871, 872) to facilitate the reflection.

As shown, body (852) also includes a light transmission element in the form of an external flat, optically transmissive surface (876) that is oriented parallel to the longitudinal axis for transmitting light beams out of body (852) and configured to face tissue between jaws (320, 322). In this regard, external flat surface (876) may be generally orthogonal to such light beams to thereby minimize refraction of the light beams transmitted therethrough. In some versions, the intersection between each light beam and flat surface (876) defines an effective sensing location (not shown) for the corresponding VCSEL (864, 865, 866) along lightbox (850). In the example shown, body (852) further includes a proximal detent (878) configured to be received by a corresponding proximal aperture (879) of cover (854) and by a corresponding distal aperture (883) of substrate (856) for removably coupling cover (854) to body (852) with the distal portion of substrate (856) captured therebetween.

In a transmission mode of operation, light beams may be transmitted from lightbox (850) through a medium (e.g., tissue or air) disposed between jaws (320, 322) and received by another lightbox (not shown), in a manner similar to that described above in connection with FIGS. 6-7. For example, light beams may be emitted from corresponding VCSELs (864, 865, 866) through respective lenses (867, 868, 869) into body (852) generally parallel to the longitudinal axis, reflected by a corresponding angled surface (871, 872) at an angle of approximately 90° to be generally orthogonal to the longitudinal axis, transmitted out of body (852) via flat surface (876), and transmitted through one or more media (e.g., tissue or air) disposed external to flat surface (876) and received by a transversely-opposed lightbox (not shown) for directing the transmitted light beams to a proximal light reader (not shown) in a manner similar to that described above in connection with FIGS. 6-7. In some versions, the transversely-opposed lightbox may be configured similarly to any one or more of lightboxes (350a, 350b, 450, 550, 650, 750) described above.

While the central axis of each VCSEL (864, 865, 866) of the present version is generally parallel to the longitudinal axis of body (852) and body (852) includes angled surfaces (871, 872) for reflecting light beams emitted from VCSELs (864, 865, 866) to be generally orthogonal to the longitudinal axis, it will be appreciated that the central axis of each VCSEL (864, 865, 866) may alternatively be generally orthogonal to the longitudinal axis. For example, each VCSEL (864, 865, 866) may be configured to emit the respective light beam directly toward flat surface (876), such that angled surfaces (871, 872) may be omitted.

III. EXAMPLES OF SYSTEM AND METHOD FOR AVOIDING PARTIAL TISSUE CUTTING

As mentioned above, end effector (180) is configured to grasp, sever, and weld/seal tissue, such as a blood vessel. In particular, jaw (184) may pivot relative to jaw (182) in order to grasp the vessel, while knife member (176) is configured to actuate within jaws (182, 184) in order to sever the vessel that is grasped between jaws (182, 184). Electrode surfaces (194, 196) may be activated while jaws (182, 184) grasp the vessel in order to weld/seal the vessel captured between jaws (182, 184). In some instances, it may be desirable to determine a position of the vessel relative to end effector (180), such as to promote full capture of the vessel jaws (182, 184) and thereby avoid partially cutting the vessel, which might otherwise result in an insufficient sealing of the vessel and/or an undesirable necked-down section of the vessel end. The method described below provides such functionality.

FIGS. 14A-14E show another exemplary end effector (916) that is operable to grasp, cut, and seal or weld tissue (e.g., a blood vessel, etc.) by applying bipolar RF energy provided by a generator (not shown) to tissue. In the example shown, end effector (916) includes a lower jaw (920) pivotally coupled with an upper jaw (not shown) via pivot couplings (924). Lower jaw (920) includes a proximal body (926) defining a slot (not shown), while the upper jaw includes proximal arms defining a slot (not shown). Lower jaw (920) also defines a central channel (934) that is configured to receive the proximal arms of the upper jaw, portions of a knife member (936), a jaw closure connecter (not shown), and a pin (not shown). The slots each slidably receive the pin, which is attached to a distal coupling portion (not shown) of the jaw closure connector. Lower jaw (920) and the upper jaw also define a knife pathway (940) configured to slidably receive knife member (936), such that knife member (936) may be retracted and advanced to cut tissue captured between lower jaw (920) and the upper jaw. Lower jaw (920) and the upper jaw each comprise a respective electrode surface (942) electrically coupled to a power source (not shown) for providing RF energy to electrode surfaces (942).

In the example shown, lower jaw (920) also comprises a recess (946) which opens toward electrode surface (942). In this regard, end effector (916) of the present version further includes at least one optical sensing device in the form of a lightbox (950) received within recess (946) of lower jaw (920). As shown, recess (946) is sized to permit lightbox (950) to be positioned adjacent to knife pathway (940) to thereby prevent lightbox (950) from interfering with advancement and retraction of knife member (936). Lightbox (950) may be fixedly secured to lower jaw (920) within recess (946) in any suitable manner. For example, lightbox (950) may include one or more coupling features such as ledges and/or press pins (not shown) configured to frictionally engage respective coupling features of recess (946). In some versions, adhesive may be applied between lightbox (950) and recess (946) to assist with securing lightbox (950) to jaw (920). To that end, the coupling features of lightbox (950) may include one or more adhesive reservoirs (not shown). Lightbox (950) may be configured similarly to any one or more of lightboxes (350a, 350b, 450, 550, 650, 750, 850) described above.

Lightbox (950) of the present version defines first, second, and third effective sensing locations (S1, S2, S3). As shown, first effective sensing location (S1) is positioned at or near a longitudinal midpoint of lower jaw (920), second effective sensing location (S2) is positioned immediately proximal of a distal end of knife pathway (940), and third effective sensing location (S3) is positioned immediately distal of the distal end of knife pathway (940). Due to the relative positioning of effective sensing locations (S1, S2, S3), lightbox (950) may be utilized for monitoring the amount of tissue, such as a vessel, captured between lower jaw (920) and the upper jaw of end effector (916). More particularly, the detection of the vessel at various effective sensing locations (S1, S2, S3) may be indicative of the amount of the vessel captures between lower jaw (920) and the upper jaw of the end effector (916), which may also be referred to as the vessel capture condition. For example, detection of the vessel may be indicative of the vessel capture condition according to the below table, wherein "Y" indicates that the vessel is detected at the effective sensing location (S1, S2, S3) and "N" indicates that the vessel is not detected at the effective sensing location (S1, S2, S3).

| S1 | S2 | S3 | Vessel Capture Condition |
|----|----|----|--------------------------|
| Y | Y | Y | Vessel partially captured for partial cutting of vessel |
| Y | Y | N | Vessel fully captured for full cutting of vessel |
| N | N | Y | Vessel partially captured for no cutting of vessel |
| Y | N | N | Vessel fully captured for full cutting of vessel |
| N | Y | Y | Vessel partially captured for partial cutting of vessel |
| N | N | N | Vessel not captured |

In some versions, lightbox (950) may be operatively coupled to a processor (not shown) configured to communicate the current vessel capture condition detected by lightbox (950) to a surgeon or other operator. In this regard, a communication that the vessel is fully captured for full cutting of the vessel or that the vessel is not captured may include a visual and/or audible indication that operation of end effector (916) may be performed safely. A communication that the vessel is partially captured for no cutting of the vessel may include a visual and/or audible indication that operation of end effector (916) may be performed with caution. And a communication that the vessel is partially captured for partial cutting of the vessel may include a visual and/or audible indication that operation of end effector (916) should not be performed.

Figure 14A:
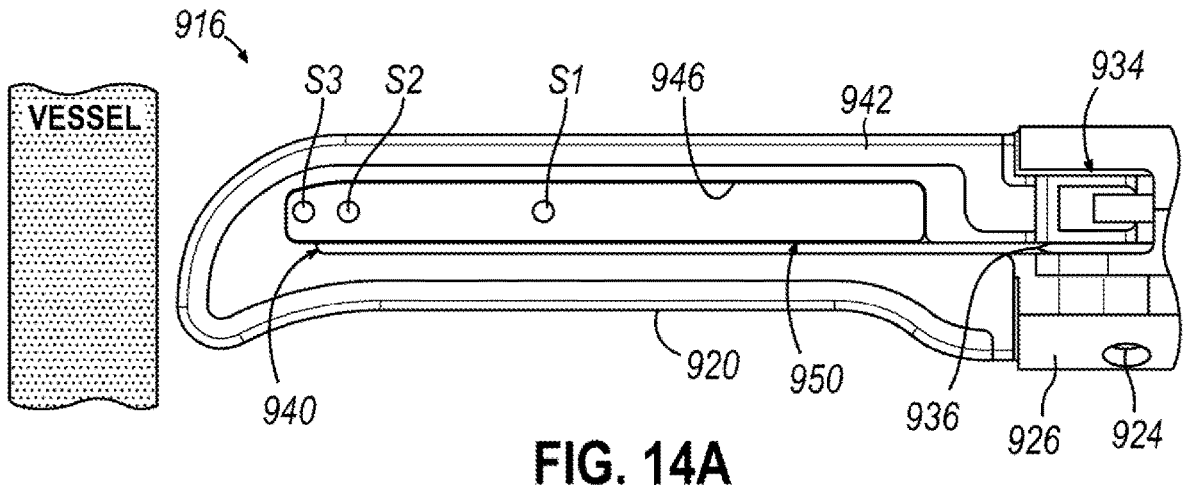
FIG. 14A depicts a top plan view of a lower jaw of another exemplary end effector having an optical sensing lightbox positioned on the lower jaw, showing a vessel positioned distal of the lower jaw such that the vessel is not detected at first, second, or third effective sensing locations of the lightbox.

For example, FIG. 14A shows the vessel not captured between lower jaw (920) and the upper jaw of end effector (916), such that the vessel is not detected at any of the effective sensing locations (S1, S2, S3) of lightbox (950). Thus, the processor may provide a visual and/or audible indication that operation of end effector (916) may be performed safely since there is no risk of partially cutting the vessel via knife member (936).

Figure 14B:
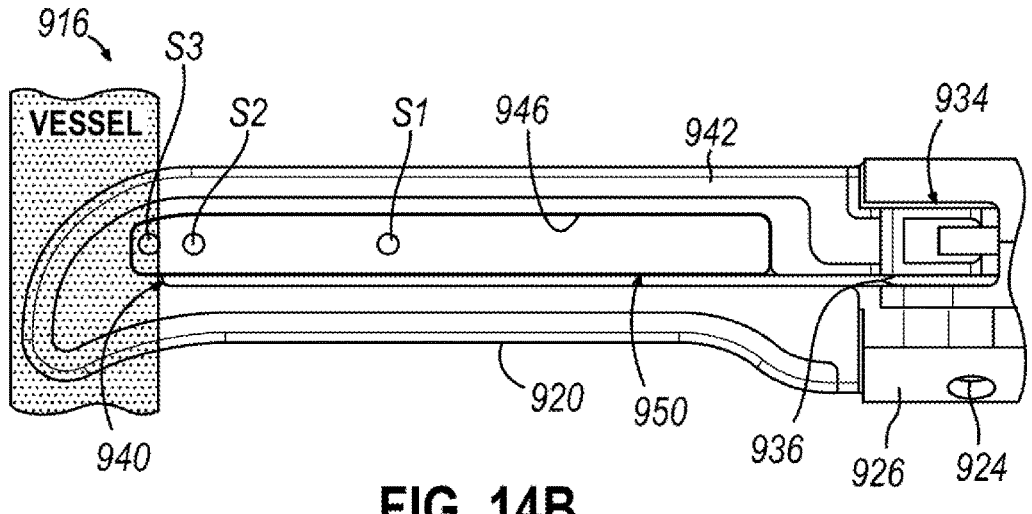
FIG. 14B depicts a top plan view of the lower jaw of FIG. 14A, showing the vessel detected at only the third effective sensing location of the lightbox of the end effector.

FIG. 14B shows the vessel partially captured between distal tips of lower jaw (920) and the upper jaw of end effector (916) distal of the distal end of knife pathway (940), such that the vessel is detected at third effective sensing location (S3) of lightbox (950) and is not detected at first or second effective sensing locations (S1, S2) of lightbox (950). Thus, the processor may provide a visual and/or audible indication that operation of end effector (916) may be performed with caution since there is minimal risk of partially cutting the vessel via knife member (936).

Figure 14C:
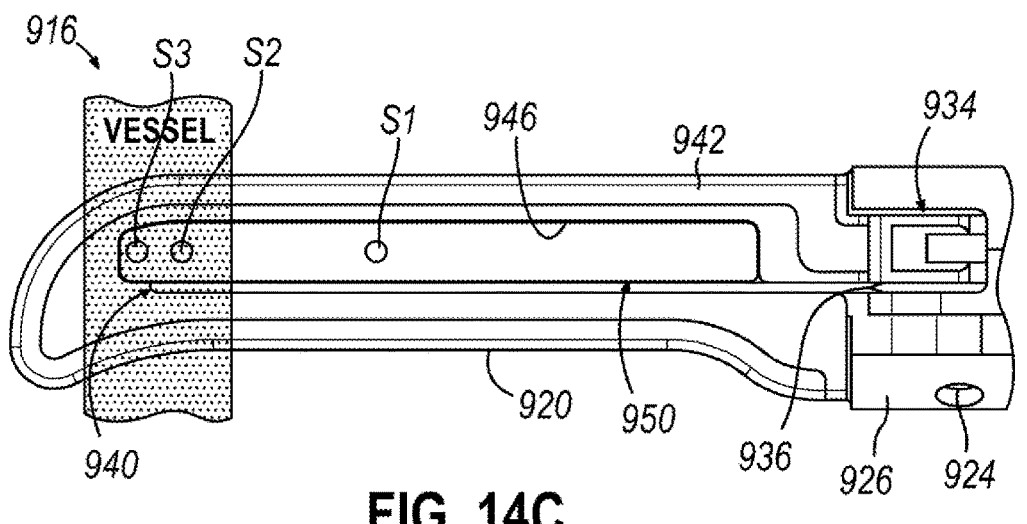
FIG. 14C depicts a top plan view of the lower jaw of FIG. 14A, showing the vessel detected at only the second and third effective sensing locations of the lightbox of the end effector.

FIG. 14C shows the vessel partially captured between lower jaw (920) and the upper jaw of end effector (916) across the distal end of knife pathway (940), such that the vessel is detected at second and third effective sensing locations (S2, S3) of lightbox (950) and is not detected at first effective sensing location (S1) of lightbox (950). Thus, the processor may provide a visual and/or audible indication that operation of end effector (916) should not be performed since there is a substantial risk of partially cutting the vessel via knife member (936).

Figure 14D:
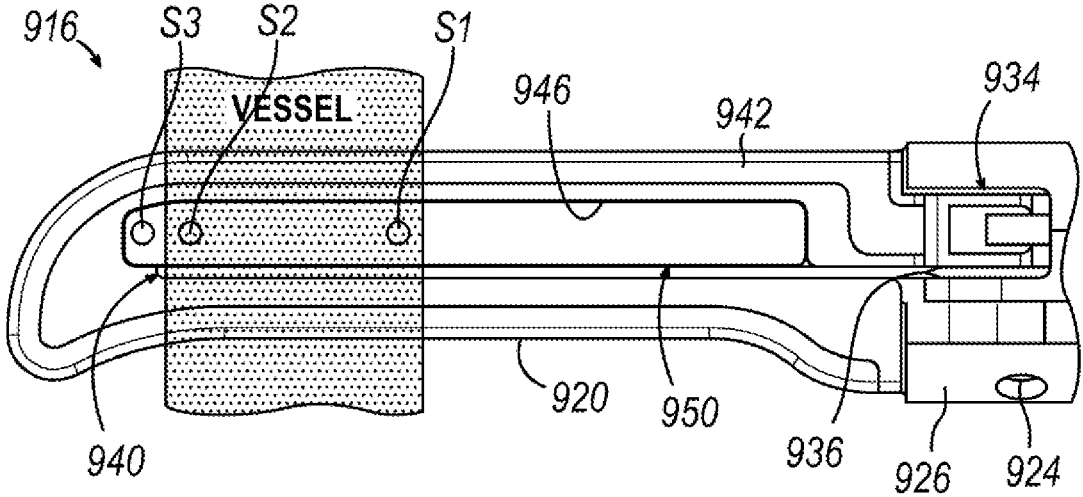
FIG. 14D depicts a top plan view of the lower jaw of FIG. 14A, showing the vessel detected at only the first and second effective sensing locations of the lightbox of the end effector.

FIG. 14D shows the vessel fully captured between lower jaw (920) and the upper jaw of end effector (916) proximal of the distal end of knife pathway (940), such that the vessel is detected at first and second effective sensing locations (S1, S2) of lightbox (950) and is not detected at third effective sensing location (S3) of lightbox (950). Thus, the processor may provide a visual and/or audible indication that operation of end effector (916) may be performed safely since there is no risk of partially cutting the vessel via knife member (936).

Figure 14E:
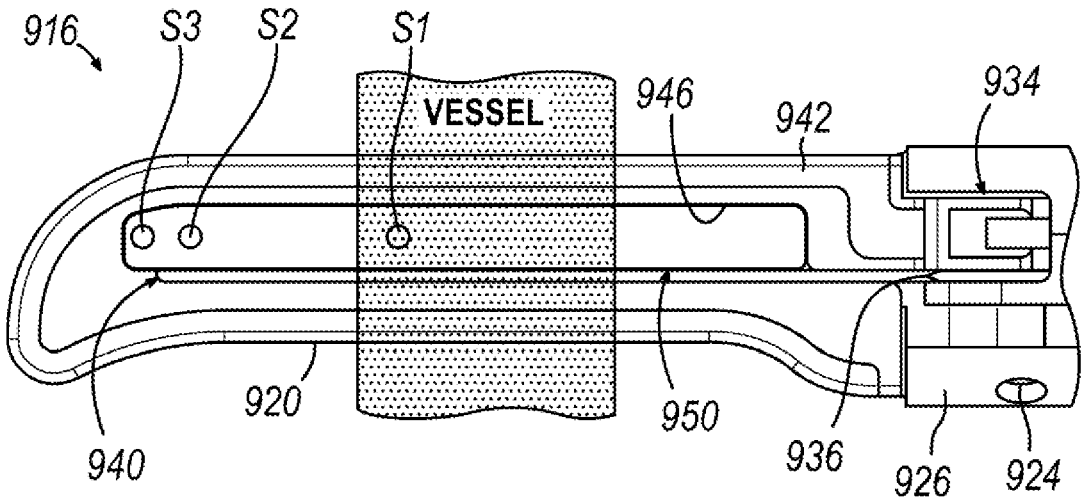
FIG. 14E depicts a top plan view of the lower jaw of FIG. 14A, showing the vessel detected at only the first effective sensing location of the lightbox of the end effector.

FIG. 14E shows the vessel fully captured between lower jaw (920) and the upper jaw of end effector (916) proximal of the distal end of knife pathway (940), such that the vessel is detected at first effective sensing location (S1) of lightbox (950) and is not detected at second or third effective sensing locations (S2, S3) of lightbox (950). Thus, the processor may provide a visual and/or audible indication that operation of end effector (916) may be performed safely since there is no risk of partially cutting the vessel via knife member (936).

It will be appreciated that first sensing location (S1) may be omitted in some versions. In such cases, lightbox (950) may utilize second and third sensing locations (S2, S3) to detect whether the vessel is partially or fully captured between lower jaw (920) and the upper jaw of end effector (916). While lightbox (950) of the present version is positioned on lower jaw (920), the same or a different lightbox may additionally or alternatively be positioned on the upper jaw of end effector (916). In other versions, lightbox (950) may be replaced with any other suitable type of sensing device(s). For example, a plurality of RF electrodes may be positioned at respective sensing locations (S1, S2, S3) for detecting the presence of the vessel thereat via impedance sensing.

IV. EXAMPLES OF SYSTEM AND METHOD FOR SCANNING TISSUE

As mentioned above, end effector (180) is configured to grasp, sever, and weld/seal tissue. In particular, jaw (184) may pivot relative to jaw (182) in order to grasp tissue, while knife member (176) is configured to actuate within jaws (182, 184) in order to sever the tissue that is grasped between jaws (182, 184). Electrode surfaces (194, 196) may be activated while jaws (182, 184) grasp the tissue in order to weld/seal the tissue captured between jaws (182, 184). In some instances, it may be desirable to identify a type of tissue captured between jaws (182, 184) and/or to determine a position of the tissue relative to end effector (180) with a minimum number of sensors that may be accommodated by end effector (180). The method described below provides such functionality.

Figure 15A:
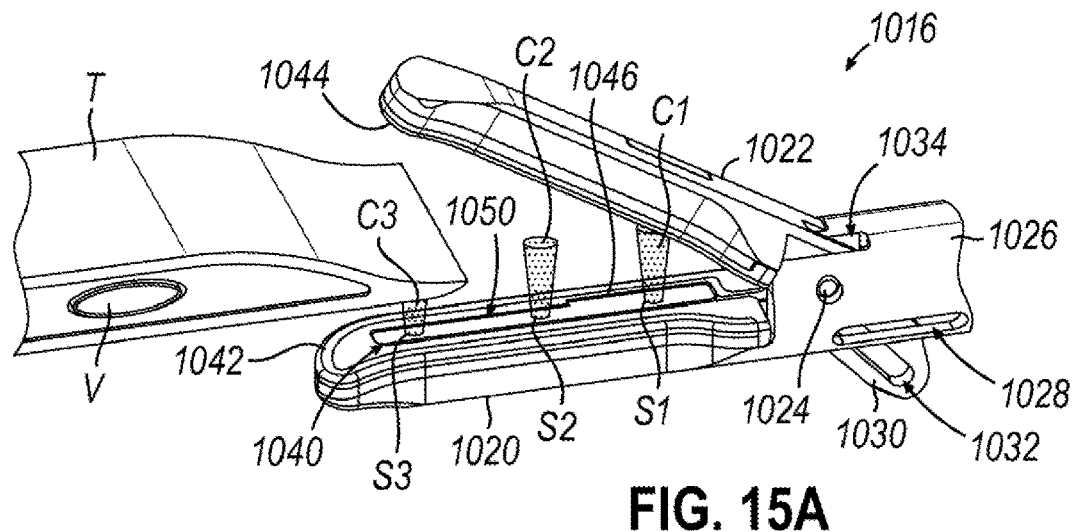
FIG. 15A depicts a perspective view of another exemplary end effector having an optical sensing lightbox positioned on a lower jaw thereof, showing a proximal portion of tissue scanned through a third cone of detection of the lightbox.
Figure 15B:
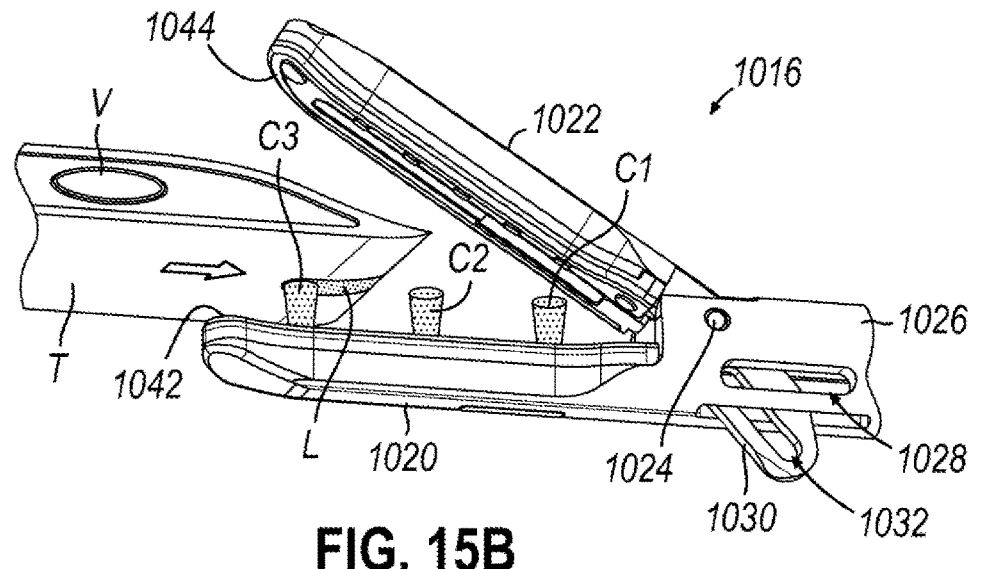
FIG. 15B depicts a perspective view of the end effector of FIG. 15A, showing the tissue advanced proximally for continuously scanning the proximal portion of the tissue through the third cone of detection of the lightbox.
Figure 15C:
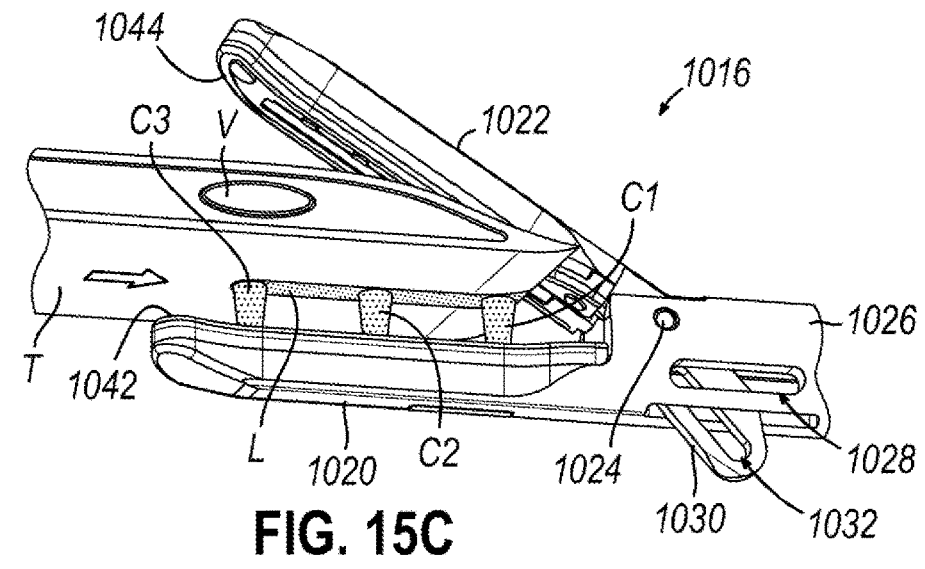
FIG. 15C depicts a perspective view of the end effector of FIG. 15A, showing the tissue advanced further proximally for continuously scanning the proximal portion of the tissue through the first, second, and third cones of detection of the lightbox.

FIGS. 15A-15C show another exemplary end effector (1016) that is operable to grasp, cut, and seal or weld tissue (T), which may include a blood vessel (V), by applying bipolar RF energy provided by a generator (not shown) to tissue (T). In the example shown, end effector (1016) includes a lower jaw (1020) pivotally coupled with an upper jaw (1022) via pivot couplings (1024). Lower jaw (1020) includes a proximal body (1026) defining a slot (1028), while upper jaw (1022) includes proximal arms (1030) defining a slot (1032). Lower jaw (1020) also defines a central channel (1034) that is configured to receive proximal arms (1030) of upper jaw (1022), portions of a knife member (not shown), a jaw closure connecter (not shown), such as jaw closure connector (160), and a pin (not shown). Slots (1028, 1032) each slidably receive the pin, which is attached to a distal coupling portion (not shown) of the jaw closure connector. Lower jaw (1020) and upper jaw (1022) also define a knife pathway (1040) configured to slidably receive the knife member, such that the knife member may be retracted and advanced to cut tissue (T) captured between jaws (1020, 1022). Lower jaw (1020) and upper jaw (1022) each comprise a respective electrode surface (1042, 1044) electrically coupled to a power source (not shown) for providing RF energy to electrode surfaces (1042, 1044).

In the example shown, lower jaw (1020) also comprises a recess (1046) which opens toward electrode surface (1042). In this regard, end effector (1016) of the present version further includes at least one optical sensing device in the form of a lightbox (1050) received within recess (1046) of lower jaw (1020). As shown, recess (1046) is sized to permit lightbox (1050) to be positioned adjacent to knife pathway (1040) to thereby prevent lightbox (1050) from interfering with advancement and retraction of the knife member. Lightbox (1050) may be fixedly secured to lower jaw (1020) within recess (1046) in any suitable manner. For example, lightbox (1050) may include one or more coupling features such as ledges and/or press pins (not shown) configured to frictionally engage respective coupling features of recess (1046). In some versions, adhesive may be applied between lightbox (1050) and recess (1046) to assist with securing lightbox (1050) to jaw (1020). To that end, the coupling features of lightbox (1050) may include one or more adhesive reservoirs (not shown). Lightbox (1050) may be configured similarly to any one or more of lightboxes (350a, 350b, 450, 550, 650, 750, 850, 950) described above.

Lightbox (1050) of the present version includes first, second, and third effective sensing locations (S1, S2, S3). As shown, first effective sensing location (S1) is proximally positioned along lower jaw (1020), second effective sensing location (S2) is intermediately positioned along lower jaw (1020), and third effective sensing location (S3) is distally positioned along lower jaw (1020). In the example shown, second effective sensing location (S2) is equally spaced apart from each of first and third effective sensing locations (S1, S3). Due to the relative positioning of effective sensing locations (S1, S2, S3), lightbox (1050) may be utilized for scanning tissue (T) captured between jaws (1020, 1022) of end effector (916). More particularly, regions of detection, such as 3-dimensional cones of detection (C1, C2, C3), extend upwardly from respective effective sensing locations (S1, S2, S3) for scanning tissue (T) as tissue (T) and jaw (1020) move relative to each other. For example, tissue (T) may be continuously scanned through one or more cones of detection (C1, C2, C3) as tissue (T) is advanced proximally between jaws (1020, 1022) and/or as jaws (1020, 1022) are advanced distally about tissue (T).

In some versions, lightbox (1050) may be operatively coupled to a processor (not shown) configured to identify the type of tissue (T) captured between jaws (1020, 1022), such as whether tissue (T) is or contains a blood vessel (V), and/or to determine a position of tissue (T) relative to end effector (180) based on spectrographic data readings obtained by scanning tissue (T) through one or more cones of detection (C1, C2, C3). For example, the processor may be configured to record the motion of tissue (T) relative to the cones of detection (C1, C2, C3) and/or to capture a series of images of tissue (T) as tissue (T) and jaw (1020) move relative to each other based on such data readings. In this regard, the processor may be configured to determine a direction in which tissue (T) is moving relative to the cones of detection (C1, C2, C3) based on any suitable identification points and/or to stitch together the various data readings to render a more comprehensive data map, which may include a long line or area of data readings. In this manner, vessel (V) may be identified by the processor as vessel (V) enters jaws (1020, 1022), and the location of vessel (V) may be continuously mapped by the processor.

More particularly, a data reading may be acquired by the processor as tissue (T) is scanned through a cone of detection (C1, C2, C3). As the data reading changes, the processor may map the data according to time and direction based on the changing data readings. When tissue (T) reaches another cone of detection (C1, C2, C3), the processor may identify similarities between the acquired data readings to stitch together the various data readings to render the data map as tissue (T) and jaw (1020) move relative to each other. In some versions, the processor may continue to map additional data during clamping of jaws (1020, 1022) as tissue (T) moves between jaws (1020, 1022). Once jaws (1020, 1022) have been clamped, the processor may determine the amount and/or type of tissue (T) within jaws (1020, 1022) by correlating the final position of the identification points relative to other positions of the identification points on the data map.

For example, FIG. 15A shows tissue (T) initially positioned between distal portions of jaws (1020, 1022) such that a proximal portion of tissue (T) is scanned through third cone of detection (C3) at third effective sensing location (S3) of lightbox (1050). Thus, the processor may begin to acquire spectrographic data readings as tissue (T) is scanned through third cone of detection (C3), record the motion of tissue (T) relative to third cone of detection (C3), capture images of tissue (T), and map the data according to time and direction based on the changing data readings.

FIG. 15B shows tissue (T) advancing proximally between jaws (1020, 1022) such that the proximal portion of tissue (T) is approaching second cone of detection (C2) while being continuously scanned through third cone of detection (C3) at third effecting sensing location (S3) of lightbox (1050). Thus, the processor may continue to acquire spectrographic data readings as tissue (T) is scanned through third cone of detection (C3), record the motion of tissue (T) relative to third cone of detection (C3), capture images of tissue (T), and map the data according to time and direction based on the changing data readings to render a data map indicative of an expanding scanned line (L) along tissue (T).

FIG. 15C shows tissue (T) advancing further proximally between jaws (1020, 1022) such that the proximal portion of tissue (T) is continuously scanned through each cone of detection (C1, C2, C3) at each effecting sensing location (S1, S2, S3) of lightbox (1050). Thus, the processor may continue to acquire spectrographic data readings as tissue (T) is scanned through each cone of detection (C1, C2, C3), record the motion of tissue (T) relative to each cone of detection (C1, C2, C3), capture images of tissue (T), and map the data according to time and direction based on the changing data readings to further render the data map indicative of the expanding scanned line (L) along tissue (T).

It will be appreciated that scanning of tissue (T) through cones of detection (C1, C2, C3) may be achieved by moving tissue (T) relative to jaw (1020) while jaw (1020) remains substantially stationary. In addition, or alternatively, scanning of tissue (T) through cones of detection (C1, C2, C3) may be achieved by sweeping jaw (1020) over a portion of tissue (T) to identify certain target anatomical structures such as blood vessel (V), one or more nerves (not shown), or other structures of interest. While lightbox (1050) of the present version is positioned on lower jaw (1020), the same or a different lightbox may additionally or alternatively be positioned on upper jaw (1022) of end effector (1016). In other versions, lightbox (1050) may be replaced with any other suitable type of sensing device(s). For example, a plurality of RF electrodes may be positioned at respective sensing locations (S1, S2, S3) for scanning tissue (T) via impedance sensing.

V. EXAMPLES OF COMBINATIONS

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a shaft assembly having a distal end; and (b) an end effector at the distal end of the shaft assembly, the end effector including: (i) a first jaw, (ii) a second jaw movably coupled relative to the first jaw for clamping tissue therebetween, and (iii) at least one lightbox for detecting the tissue, wherein the at least one lightbox includes: (A) a housing having at least one optically transmissive surface configured to face the tissue, and (B) at least one of an illuminating element or a light receiving element, wherein the at least one of an illuminating element or a light receiving element is secured to the housing.

Example 2

The surgical instrument of Example 1, wherein the at least one lightbox is positioned on at least one of the first or second jaws.

Example 3

The surgical instrument of Example 2, wherein the at least one lightbox is configured to transmit light to the tissue for reflection by the tissue back to the at least one lightbox.

Example 4

The surgical instrument of any one or more of Examples 2 through 3, wherein the at least one lightbox includes a first lightbox positioned on the first jaw and a second lightbox positioned on the second jaw.

Example 5

The surgical instrument of Example 4, wherein the first lightbox is configured to transmit light through the tissue, wherein the second lightbox is configured to receive the light transmitted through the tissue.

Example 6

The surgical instrument of any one or more of Examples 1 through 5, wherein the at least one lightbox includes at least one light reflection element.

Example 7

The surgical instrument of Example 6, wherein the at least one light reflection element is configured to reflect light at an angle of between approximately 30° and approximately 90°.

Example 8

The surgical instrument of any one or more of Examples 6 through 7, wherein the at least one light reflection element includes at least one surface oriented at an oblique angle relative to a longitudinal axis of the at least one lightbox.

Example 9

The surgical instrument of any one or more of Examples 6 through 8, wherein the at least one light reflection element includes at least one parabolic surface.

Example 10

The surgical instrument of any one or more of Examples 1 through 9, wherein the housing includes a translucent body.

Example 11

The surgical instrument of any one or more of Examples 1 through 10, wherein the at least one lightbox includes at least one lens configured to condition light.

Example 12

The surgical instrument of any one or more of Examples 1 through 11, wherein the at least one of an illuminating element or a light receiving element includes at least one illuminating element, wherein the at least one lightbox includes at least one port for receiving the at least one illuminating element.

Example 13

The surgical instrument of any one or more of Examples 1 through 12, wherein the at least one of an illuminating element or a light receiving element includes at least one optical fiber.

Example 14

The surgical instrument of any one or more of Examples 1 through 13, wherein the at least one of an illuminating element or a light receiving element includes at least one illuminating element, wherein the at least one illuminating element includes at least one vertical-cavity surface-emitting laser (VCSEL).

Example 15

The surgical instrument of any one or more of Examples 1 through 14, wherein the first and second jaws define a knife pathway for directing a knife member therealong, wherein the at least one lightbox is positioned adjacent to the knife pathway.

Example 16

A surgical system, comprising: (a) a surgical instrument, comprising: (i) a shaft assembly having a distal end, and (ii) an end effector at the distal end of the shaft assembly, the end effector including: (A) a first jaw, (B) a second jaw movably coupled relative to the first jaw for clamping tissue therebetween, and (C) at least one lightbox for detecting the tissue, wherein the at least one lightbox defines a plurality of effective sensing locations; and (b) a processor operatively coupled to the at least one lightbox, wherein the processor is configured to determine a status of the tissue based on detection of the tissue at one or more of the plurality of effective sensing locations of the at least one lightbox.

Example 17

The surgical system of Example 16, wherein the first and second jaws define a knife pathway for directing a knife member therealong, wherein the plurality of effective sensing locations includes a first effective sensing location disposed proximal of a distal end of the knife pathway and a second effective sensing location disposed distal of the distal end of the knife pathway.

Example 18

The surgical system of any one or more of Examples 16 through 17, wherein the at least one lightbox includes: (I) a housing having at least one optically transmissive surface configured to face the tissue, and (II) at least one of an illuminating element or a light receiving element, wherein the at least one of an illuminating element or a light receiving element is secured to the housing.

Example 19

A surgical system, comprising: (a) a surgical instrument, comprising: (i) a shaft assembly having a distal end, and (ii) an end effector at the distal end of the shaft assembly, the end effector including: (A) a first jaw, (B) a second jaw movably coupled relative to the first jaw for clamping tissue therebetween, and (C) at least one lightbox for detecting the tissue, wherein the at least one lightbox defines a plurality of effective sensing locations; and (b) a processor operatively coupled to the at least one lightbox, wherein the processor is configured to render a data map of the tissue based on scanning of the tissue at one or more of the plurality of effective sensing locations of the at least one lightbox.

Example 20

The surgical system of Example 19, wherein the at least one lightbox includes: (I) a housing having at least one optically transmissive surface configured to face the tissue, and (II) at least one of an illuminating element or a light receiving element, wherein the at least one of an illuminating element or a light receiving element is secured to the housing.

Example 21

A method, comprising: (a) transmitting light toward tissue from a first lightbox of an end effector of a surgical instrument; and (b) receiving the light from the tissue to detect the tissue.

Example 22

The method of Example 21, wherein the act of receiving is performed by the first lightbox, wherein the light is reflected by the tissue back to the first lightbox.

Example 23

The method of Example 21, wherein the act of receiving is performed by a second lightbox of the end effector, wherein the light is transmitted through the tissue to the second lightbox.

Example 24

The method of any one or more of Examples 21-23, wherein the first lightbox defines a plurality of effective sensing locations, the method further comprising determining a status of the tissue based on detection of the tissue at one or more of the plurality of effective sensing locations of the first lightbox.

Example 25

The method of any one or more of Examples 21-24, wherein the first lightbox defines a plurality of effective sensing locations, the method further comprising rendering a data map of the tissue based on scanning of the tissue at one or more of the plurality of effective sensing locations of the first lightbox.

Example 26

A surgical instrument, comprising: (a) a shaft assembly having a distal end; and (b) an end effector at the distal end of the shaft assembly, the end effector including: (i) a first jaw, (ii) a second jaw movably coupled relative to the first jaw for clamping tissue therebetween, and (iii) at least one lightbox for detecting the tissue, wherein the at least one lightbox includes: (A) a housing having at least one optically transmissive surface configured to face the tissue, (B) at least one of an illuminating element or a light receiving element, wherein the at least one of an illuminating element or a light receiving element is secured to the housing, and (C) at least one optically reflective angled surface configured to redirect light transmitted from or toward the at least one of an illuminating element or a light receiving element.

Example 27

A surgical instrument, comprising: (a) a shaft assembly having a distal end; and (b) an end effector at the distal end of the shaft assembly, the end effector including: (i) a first jaw, (ii) a second jaw movably coupled relative to the first jaw for clamping tissue therebetween, and (iii) at least one lightbox for detecting the tissue, wherein the at least one lightbox includes: (A) a housing having at least one optically transmissive surface configured to face the tissue, (B) at least one of an illuminating element or a light receiving element, wherein the at least one of an illuminating element or a light receiving element is secured to the housing, and (C) at least one lens configured to condition light transmitted from or toward the at least one of an illuminating element or a light receiving element, wherein the at least one lens is secured to the housing.

Example 28

A surgical instrument, comprising: (a) a shaft assembly having a distal end; and (b) an end effector at the distal end of the shaft assembly, the end effector including: (i) a first jaw, (ii) a second jaw movably coupled relative to the first jaw for clamping tissue therebetween, and (iii) at least one lightbox for detecting the tissue, wherein the at least one lightbox includes: (A) a housing having at least one optically transmissive surface configured to face the tissue, (B) at least one of an illuminating element or a light receiving element, wherein the at least one of an illuminating element or a light receiving element is secured to the housing, and (C) at least one optically reflective parabolic surface configured to redirect and condition light transmitted from or toward the at least one of an illuminating element or a light receiving element.

Example 29

A surgical instrument, comprising: (a) a shaft assembly having a distal end; and (b) an end effector at the distal end of the shaft assembly, the end effector including: (i) a first jaw, (ii) a second jaw movably coupled relative to the first jaw for clamping tissue therebetween, and (iii) at least one lightbox for detecting the tissue, wherein the at least one lightbox includes: (A) a housing having at least one optically transmissive surface configured to face the tissue, (B) at least one of an illuminating element or a light receiving element, wherein the at least one of an illuminating element or a light receiving element is secured to the housing, (C) at least one optically reflective parabolic surface configured to redirect and condition light transmitted from or toward the at least one of an illuminating element or a light receiving element, and (D) at least one raw optical fiber configured to transmit light directly to the at least one optically transmissive surface or to receive light directly from the at least one optically transmissive surface.

VI. MISCELLANEOUS

It should be understood that any of the versions of the instruments described herein may include various other features in addition to or in lieu of those described above. By way of example only, any of the devices herein may also include one or more of the various features disclosed in any of the various references that are incorporated by reference herein. Various suitable ways in which such teachings may be combined will be apparent to those of ordinary skill in the art.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Additionally, any one or more of the teachings herein may be combined with any one or more of the teachings of U.S. patent application Ser. No. 17,489,894, entitled "Electrosurgical Instrument with Fiber Optic Rotary Coupling," filed on Sept. 30, 2021, published as U.S. Pat. Pub. No. 2023/100459; and U.S. patent application Ser No. 17,490,045, entitled "Electrosurgical System with Optical Sensor Electronics," filed on Sept. 30, 2021, published as U.S. Pat. Pub. No. 2023/0101623. The disclosure of each of these US patent documents is incorporated by reference herein.

It should be appreciated that any patent, publication, or other disclosure material, in whole or in part, that is said to be incorporated by reference herein is incorporated herein only to the extent that the incorporated material does not conflict with existing definitions or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein, in its entirety.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A surgical instrument, comprising:
(a) a shaft assembly having a distal end; and

(b) an end effector at the distal end of the shaft assembly, the end effector longitudinally extending along a longitudinal axis and including:

(i) a first jaw, (ii) a second jaw movably coupled relative to the first jaw for clamping tissue therebetween, wherein the second jaw is configured to selectively and transversely move toward the longitudinal axis and thereby toward a closed configuration with the first jaw for clamping the tissue therebetween and (iii) at least one lightbox for detecting the tissue, wherein the at least one lightbox includes:

(A) a housing having at least one optically transmissive surface configured to face the tissue, (B) a first illuminating element secured to the housing, (C) a second illuminating element secured to the housing, (D) a first optically reflective angled surface configured to redirect light transmitted from the first illuminating element, and (E) a second optically reflective angled surface configured to redirect light transmitted from the second illuminating element, wherein the first optically reflective angled surface is closer to the longitudinal axis in a transverse direction than the second optically reflective angled surface in the transverse direction, wherein at least one of the first or second jaws includes an electrode surface configured to apply radiofrequency energy to the tissue, wherein the at least one of the first or second jaws includes a recess opening toward the electrode surface, wherein the at least one lightbox is received within the recess.

2. The surgical instrument of claim 1, wherein the at least one lightbox is configured to transmit light to the tissue for reflection by the tissue back to the at least one lightbox.

3. The surgical instrument of claim 1, wherein the at least one lightbox includes a first lightbox positioned on the first jaw and a second lightbox positioned on the second jaw.

4. The surgical instrument of claim 3, wherein the first lightbox is configured to transmit light through the tissue, wherein the second lightbox is configured to receive the light transmitted through the tissue.

5. The surgical instrument of claim 1, wherein each of the first and second optically reflective angled surfaces is configured to reflect light at an angle of between approximately 30° and approximately 90°.

6. The surgical instrument of claim 1, wherein at least one of the first and second optically reflective angled surfaces is oriented at an oblique angle relative to the longitudinal axis.

7. The surgical instrument of claim 1, wherein at least one of the first and second optically reflective angled surfaces includes at least one parabolic surface.

8. The surgical instrument of claim 1, wherein the housing includes a translucent body.

9. The surgical instrument of claim 1, wherein the at least one lightbox includes at least one lens configured to condition light.

10. The surgical instrument of claim 1, wherein the at least one lightbox includes at least one port for receiving the first illuminating element.

11. The surgical instrument of claim 1, wherein the first illuminating element includes at least one optical fiber.

12. The surgical instrument of claim 1, wherein the first illuminating element includes at least one vertical-cavity surface-emitting laser (VCSEL).

13. The surgical instrument of claim 1, wherein the first and second jaws define a knife pathway for directing a knife member therealong, wherein the at least one lightbox is positioned adjacent to the knife pathway.

14. The surgical instrument of claim 1, wherein the first and second optically reflective angled surfaces are unitarily formed together.

15. The surgical instrument of claim 1, wherein the second optically reflective angled surface is longitudinally closer to the shaft assembly than the first optically reflective angled surface.

16. A surgical instrument, comprising:

(a) a shaft assembly having a distal end; and (b) an end effector at the distal end of the shaft assembly, the end effector including:

(i) a first jaw, (ii) a second jaw movably coupled relative to the first jaw for clamping tissue therebetween, and (iii) at least one lightbox for detecting the tissue, wherein the at least one lightbox includes:

(A) a housing having at least one optically transmissive surface configured to face the tissue, (B) at least one of an illuminating element or a light receiving element, wherein the at least one of an illuminating element or a light receiving element is secured to the housing, (C) a first optically reflective angled surface configured to redirect light, and (D) a second optically reflective angled surface configured to redirect light, wherein the housing, the first optically reflective angled surface, and the second optically reflective angled surface are integrally formed together as a unitary piece.

17. The surgical instrument of claim 16, wherein the at least one lightbox further includes a third optically reflective angled surface configured to redirect light, wherein the housing, the first optically reflective angled surface, the second optically reflective angled surface, and the third optically reflective angled surface are integrally formed together as a unitary piece.

18. A surgical instrument, comprising:

(a) a shaft assembly having a distal end; and (b) an end effector at the distal end of the shaft assembly, the end effector including:

(i) a first jaw, (ii) a second jaw movably coupled relative to the first jaw for clamping tissue therebetween, and (iii) a first lightbox for detecting the tissue including:

(A) a first distal body being formed of a transparent material or a translucent material, and (B) a first proximal body having at least one of an illuminating element or a light receiving element, wherein the first proximal body is secured to the first distal body, wherein the first lightbox is received within the first jaw, and (iv) a second lightbox for detecting the tissue including:

(A) a second distal body being formed of a transparent material or a translucent material, and (B) a second proximal body having at least one of an illuminating element or a light receiving element, wherein the second proximal body is secured to the second distal body, wherein the second lightbox is received within the second jaw.

19. The surgical instrument of claim 18, wherein the first distal body is integrally formed as a unitary piece.

20. The surgical instrument of claim 19, wherein the second distal body is integrally formed as another unitary piece.

* * * * *